(12) United States Patent
Kim et al.

(10) Patent No.: US 7,560,265 B2
(45) Date of Patent: Jul. 14, 2009

(54) COMPOSITIONS FOR REGULATION OF TUMOR NECROSIS FACTOR-ALPHA

(75) Inventors: Soo-Hyun Kim, Aurora, CO (US); Charles A. Dinarello, Boulder, CO (US); Tania Azam, Denver, CO (US)

(73) Assignee: The Regents of the University of Colorado, a body corporate, Boulder, CO (US)

( * ) Notice: Subject to any disclaimer, the term of this patent is extended or adjusted under 35 U.S.C. 154(b) by 0 days.

(21) Appl. No.: 10/578,943

(22) PCT Filed: Nov. 12, 2004

(86) PCT No.: PCT/US2004/037578

§ 371 (c)(1), (2), (4) Date: Nov. 9, 2006

(87) PCT Pub. No.: WO2005/047478

PCT Pub. Date: May 26, 2005

(65) Prior Publication Data

US 2007/0071719 A1     Mar. 29, 2007

Related U.S. Application Data

(60) Provisional application No. 60/519,818, filed on Nov. 12, 2003.

(51) Int. Cl.
C12P 21/02 (2006.01)
C12N 1/20 (2006.01)
C12N 15/00 (2006.01)
C12N 15/63 (2006.01)

(52) U.S. Cl. .................. 435/252.3; 435/320.1; 536/23.5

(58) Field of Classification Search ........................ None
See application file for complete search history.

(56) References Cited

U.S. PATENT DOCUMENTS

| | | | |
|---|---|---|---|
| 6,277,969 B1 | 8/2001 | Le et al. ..................... 536/23.1 |
| 6,448,380 B2 | 9/2002 | Rathjen et al. ......... 530/388.23 |
| 6,572,852 B2 | 6/2003 | Smith et al. ................ 424/85.2 |
| 6,605,280 B1 | 8/2003 | Novick et al. ............ 424/184.1 |
| 6,706,491 B1 | 3/2004 | Chang et al. .................. 435/29 |
| 6,989,262 B2 | 1/2006 | Bejanin et al. ............... 435/226 |
| 2003/0073623 A1* | 4/2003 | Drmanac et al. .............. 514/12 |
| 2003/0087270 A1 | 5/2003 | Schlegel et al. ................. 435/6 |
| 2003/0092616 A1 | 5/2003 | Matsuda et al. ................ 514/12 |
| 2003/0148316 A1 | 8/2003 | Lipford et al. .................. 435/6 |
| 2003/0154032 A1 | 8/2003 | Pittman et al. ................ 702/20 |
| 2005/0048490 A1 | 3/2005 | Azimzai et al. ................. 435/6 |
| 2005/0130145 A1 | 6/2005 | Yue et al. ....................... 435/6 |
| 2005/0208496 A1 | 9/2005 | Ohtani et al. ................... 435/6 |
| 2006/0088532 A1 | 4/2006 | Alitalo et al. ............. 424/145.1 |

FOREIGN PATENT DOCUMENTS

| | | | |
|---|---|---|---|
| EP | 1487857 | | 12/2004 |
| WO | WO/94/01548 | * | 1/1994 |
| WO | WO/0164886 | * | 7/2001 |
| WO | WO 01/64886 | | 9/2001 |
| WO | WO 02/059260 | | 8/2002 |
| WO | WO 02/083898 | | 10/2002 |
| WO | WO/02/083898 | * | 10/2002 |
| WO | WO/02/094864 | * | 11/2002 |
| WO | WO 02/096943 | | 12/2002 |
| WO | WO 03/080640 | | 10/2003 |
| WO | WO 2005/016962 | | 2/2005 |
| WO | WO 2006/071088 | | 7/2006 |

OTHER PUBLICATIONS

National Institutes of Health, Mammalian Gene Collection (MGC) entry: AGENCOURT_10614895 NIH_MGC_127 Homo sapiens cDNA clone Image: 6745305 available Oct. 18, 2002.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Bork, A. Powers and pitfalls in sequence analysis: the 70% hurdle. Genome Res 10: 398-400, 2000.*
Skolnick et al. From genes to protein structure and function: novel applications of computational approaches in the genomic era. Trends in Biotech 18(1): 34-39, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Banda et al., "Mechanisms of effects of complement inhibition in murine collagen-induced arthritis," Arthritis Rheum, 46:3065, 2002.
Banda et al., "Mechanisms of inhibition of collagen-induced arthritis by murine IL-18 binding protein," J Immunol, 170:2100-2105, 2003.
Bendele et al., "Combination benefit of treatment with the cytokine inhibitors interleukin-1 receptor antagonist and PEGylated soluble tumor necrosis factor receptor type I in animal models of rheumatoid arthritis," Arthritis Rheum, 43:2648-2659, 2000.
Bernot et al., "A transcriptional map of the FMF region" Genomics, 50:147-160, 1998.
Cohen, "Systemic Autoimmunity," in Paul (ed.) Fundamental Immunology, Lippincott-Raven Publishers: Philadelphia, pp. 1067-1088, 1999.
Dahl et al., "Identification of a novel gene expressed in activated natural killer cells and T cells," J Immunol, 148:597-603, 1992.

(Continued)

Primary Examiner—Lorraine Spector
Assistant Examiner—Elly-Gerald Stoica
(74) Attorney, Agent, or Firm—Medlen & Carroll, LLP

(57) ABSTRACT

The present invention relates to compositions relating a nucleic acid encoding an interleukin 18-inducible cytokine termed tumor necrosis factor-alpha inducing factor (TAIF) or interleukin-32 (IL-32). In particular, the present invention provides vectors for expressing proteins useful for treating autoimmune diseases and cancer, in part by regulation of tumor necrosis factor-alpha expression.

5 Claims, 15 Drawing Sheets

OTHER PUBLICATIONS

Davis et al., "Treatment of rheumatoid arthiritis with PEGylated recombinant human soluble tumour necrosis factor receptor type I: a clinical update," *Ann Rhem Dis*, 59Suppl1 :i41-3, 2000.

Faggioni et al., "IL-18-binding protein protects against lipopolysaccharide-induced lethality and prevents the development of Fas/Fas ligand-mediated models of liver disease in mice," *J Immunol*, 167:5913-5920, 2001.

Firestein, "Rheumatoid Arthritis," in *Scientific American Medicine*, 2000.

Panelli et al., "Gene-expression profiling of the response of peripheral blood mononuclear cells and melanoma metastases to systemic IL-2 administration" *Genome Biol*, 3(7):research0035.1-0035.17, 2002.

Gracie et al., "A proinflammatory role for IL-18 in rheumatoid arthritis," *J Clin Invest*, 104:1393-1401, 1999.

Steed et al., "Inactivation of TNF signaling by rationally designed dominant-negative TNF variants,"*Science*, 301:1895-1898, 2003.

GenBank Accession No. AAH09401 GI:14424787 (2002).
GenBank Accession No. AAH18782 GI:17511868 (2002).
GenBank Accession No. AAS80144 GI:46095218 (2005).

Dinarello and Kim, "IL-32, a novel cytokine with a possible role in disease," *Ann Rheum Dis*, 65(Suppl III):iii61-iii64, 2006.

Joosten et al., "IL-32, a proinflammatory cytokine in rheumatoid arthritis," *Proc Natl Acad Sci USA*, 103:3298-3303, 2006.

Kim et al., "Interleukin-32: A cytokine and inducer of TNFα," *Immunity*, 22:131-142, 2005.

Neto et al., "Shotgun sequencing of the human transcriptome with ORF expressed sequence tags," *Proc Natl Acad Sci USA*, 97:3491-3496, 2000.

Plater-Zyberk et al., "Therapeutic effect of neutralizing endogenous IL-18 activity in the collagen-induced model of arthritis," *J Clin Invest*, 108:1825-1832, 2001.

Strausberg et al., "Generation and initial analysis of more than 15,000 full-length human and mouse cDNA sequence," *Proc Natl Acad Sci USA*, 99:16899-16903, 2002.

* cited by examiner

A
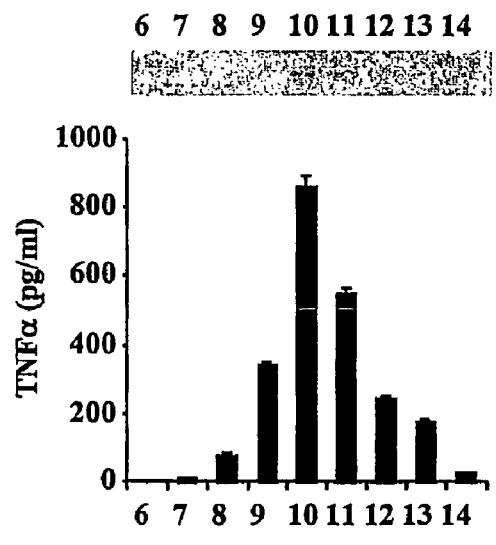
B
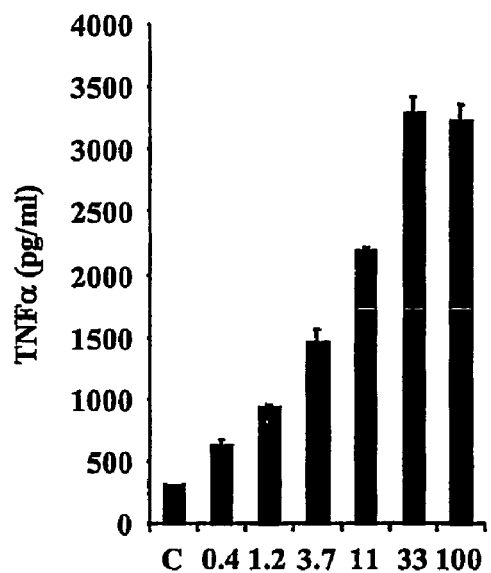
C
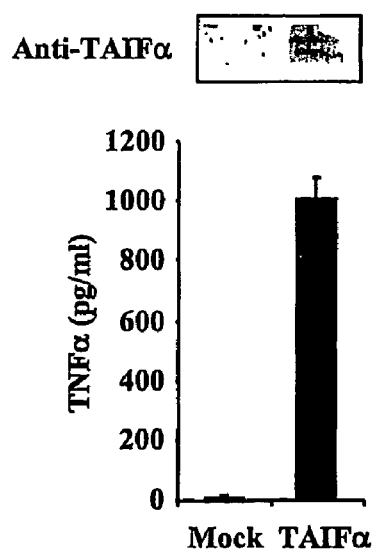
Fig. 2

```
IL-32α   ATGTGCTTCCCGAAGGTCCTCTCTGATGACATGAAGAAGCTGAAGGCCCGAATG------
IL-32β   ATGTGCTTCCCGAAGGTCCTCTCTGATGACATGAAGAAGCTGAAGGCCCGAATG------
IL-32γ   ATGTGCTTCCCGAAGGTCCTCTCTGATGACATGAAGAAGCTGAAGGCCCGAATGGTAATG
IL-32δ   ------------------------------ATGAAGAAGCTGAAGGCCCGAATG------

IL-32α   ------------------------------------------------------------
IL-32β   ------------------------------------------------------------
IL-32γ   CTCCTCCCTACTTCTGCTCAGGGGTTGGGGGCCTGGGTCTCAGCGTGTGACACTGAGGAC
IL-32δ   ------------------------------------------------------------

IL-32α   ------------------------------------------------------------
IL-32β   ------------------------------------------------------------
IL-32γ   ACTGTGGGACACCTGGGACCCTGGAGGGACAAGGATCCGGCCCTTTGGTGCCAACTCTGC
IL-32δ   ------------------------------------------------------------

IL-32α   -----------CACCAGGCTATAGAAAGATTTTATGATAAAATGCAAAATGCAGAATCA
IL-32β   -----------CACCAGGCCATAGAAAGATTTTATGATAAAATGCAAAATGCAGAATCA
IL-32γ   CTCTCTTCACAGCACCAGGCCATAGAAAGATTTTATGATAAAATGCAAAATGCAGAATCA
IL-32δ   -----------CACCAGGCCATAGAAAGATTTTATGATAAAATGCAAAATGCAGAATCA

IL-32α   GGACGTGGACAGGTGATGTCGAGCCTGGCAGAGCTGGAGGACGACTTCAAAGAGGGCTAC
IL-32β   GGACGTGGACAGGTGATGTCGAGCCTGGCAGAGCTGGAGGACGACTTCAAAGAGGGCTAC
IL-32γ   GGACGTGGACAGGTGATGTCGAGCCTGGCAGAGCTGGAGGACGACTTCAAAGAGGGCTAC
IL-32δ   GGACGTGGACAGGTGATGTCGAGCCTGGCAGAGCTGGAGGACGACTTCAAAGAGGGCTAC

IL-32α   CTGGAGACAGTGGCGGCTTATTATGAGGAGCAGCACCCAGAGCTCACTCCTCTACTTGAA
IL-32β   CTGGAGACAGTGGCGGCTTATTATGAGGAGCAGCACCCAGAGCTCACTCCTCTACTTGAA
IL-32γ   CTGGAGACAGTGGCGGCTTATTATGAGGAGCAGCACCCAGAGCTCACTCCTCTACTTGAA
IL-32δ   CTGGAGACAGTGGCGGCTTATTATGAGGAGCAGCACCCAGAGCTCACTCCTCTACTTGAA
```

Fig. 3A

```
IL-32α    AAAGAAAGAGATGGATTACGGTGCCGAGGCAACAGATCCCCTGTCCCGGATGTTGAGGAT
IL-32β    AAAGAAAGAGATGGATTACGGTGCCGAGGCAACAGATCCCCTGTCCCGGATGTTGAGGAT
IL-32γ    AAAGAAAGAGATGGATTACGGTGCCGAGGCAACAGATCCCCTGTCCCGGATGTTGAGGAT
IL-32δ    AAAGAAAGAGATGGATTACGGTGCCGAGGCAACAGATCCCCTGTCCCGGATGTTGAGGAT

IL-32α    CCCGCAACCGAGGAGCCTGGGGAGAGCTTTTGTGACAAG---------------------
IL-32β    CCCGCAACCGAGGAGCCTGGGGAGAGCTTTTGTGACAAGGTCATGAGATGGTTCCAGGCC
IL-32γ    CCCGCAACCGAGGAGCCTGGGGAGAGCTTTTGTGACAAGGTCATGAGATGGTTCCAGGCC
IL-32δ    CCCGCAACCGAGGAGCCTGGGGAGAGCTTTTGTGACAAGGTCATGAGATGGTTCCAGGCC

IL-32α    ------------------------------------------------------------
IL-32β    ATGCTGCAGCGGCTGCAGACCTGGTGGCACGGGGTTCTGGCCTGGGTGAAGGAGAAGGTG
IL-32γ    ATGCTGCAGCGGCTGCAGACCTGGTGGCACGGGGTTCTGGCCTGGGTGAAGGAGAAGGTG
IL-32δ    ATGCTGCAGCGGCTGCAGACCTGGTGGCACGGGGTTCTGGCCTGGGTGAAGGAGAAGGTG

IL-32α    ------------------------------------------------------------
IL-32β    GTGGCCCTGGTCCATGCAGTGCAGGCCCTCTGGAAACAGTTCCAGAGTTTCTGCTGCTCT
IL-32γ    GTGGCCCTGGTCCATGCAGTGCAGGCCCTCTGGAAACAGTTCCAGAGTTTCTGCTGCTCT
IL-32δ    GTGGCCCTGGTCCATGCAGTGCAGGCCCTCTGGAAACAGTTCCAGAGTTTCTGCTGCTCT

IL-32α    ------------------------------TCCTACGGAGCCCCACGGGGGGACAAGGAG
IL-32β    CTGTCAGAGCTCTTCATGTCCTCTTTCCAGTCCTACGGAGCCCCACGGGGGGACAAGGAG
IL-32γ    CTGTCAGAGCTCTTCATGTCCTCTTTCCAGTCCTACGGAGCCCCACGGGGGGACAAGGAG
IL-32δ    CTGTCAGAGCTCTTCATGTCCTCTTTCCAGTCCTACGGAGCCCCACGGGGGGACAAGGAG

IL-32α    GAGCTGACACCCCAGAAGTGCTCTGAACCCCAATCCTCAAAATGA
IL-32β    GAGCTGACACCCCAGAAGTGCTCTGAACCCCAATCCTCAAAATGA
IL-32γ    GAGCTGACACCCCAGAAGTGCTCTGAACCCCAATCCTCAAAATGA
IL-32δ    GAGCTGACACCCCAGAAGTGCTCTGAACCCCAATCCTCAAAATGA
```

```
              1                                  Myr
IL-32α    MCFPKVLSDDMKKLKARM----------------------------------------
IL-32β    MCFPKVLSDDMKKLKARM----------------------------------------
IL-32γ    MCFPKVLSDDMKKLKARMVMLLPTSAQGLGAWVSACDTEDTVGHLGPWRDKDPALWCQLC
IL-32δ    ----------MKKLKARM----------------------------------------

61                                 Myr
IL-32α    ----HQAIERFYDKMQNAESGRGQVMSSLAELEDDFKEGYLETVAAYYEEQHPELTPLLE
IL-32β    ----HQAIERFYDKMQNAESGRGQVMSSLAELEDDFKEGYLETVAAYYEEQHPELTPLLE
IL-32γ    LSSQHQAIERFYDKMQNAESGRGQVMSSLAELEDDFKEGYLETVAAYYEEQHPELTPLLE
IL-32δ    ----HQAIERFYDKMQNAESGRGQVMSSLAELEDDFKEGYLETVAAYYEEQHPELTPLLE

121        Gly
IL-32α    KERDGLRCRGNRSPVPDVEDPATEEPGESFCDK---------------------------
IL-32β    KERDGLRCRGNRSPVPDVEDPATEEPGESFCDKVMRWFQAMLQRLQTWWHGVLAWVKEKV
IL-32γ    KERDGLRCRGNRSPVPDVEDPATEEPGESFCDKVMRWFQAMLQRLQTWWHGVLAWVKEKV
IL-32δ    KERDGLRCRGNRSPVPDVEDPATEEPGESFCDKVMRWFQAMLQRLQTWWHGVLAWVKEKV

181                                Myr
IL-32α    ------------------------------SYGAPRGDKEELTPQKCSEPQSSK
IL-32β    VALVHAVQALWKQFQSFCCSLSELFMSSFQSYGAPRGDKEELTPQKCSEPQSSK
IL-32γ    VALVHAVQALWKQFQSFCCSLSELFMSSFQSYGAPRGDKEELTPQKCSEPQSSK
IL-32δ    VALVHAVQALWKQFQSFCCSLSELFMSSFQSYGAPRGDKEELTPQKCSEPQSSK
```

B

```
              1
huIL-32β   MCFPKVLSDDMKKLKARMHQAIERFYDKMQNAESGRGQVMSSLAELEDDFKEGYLETVAA
EqIL-32    MGYPKTSREDNERWKIRFHSTLDRWLDDIEVQSQGEEQVDLGLEDLEEKFSENILDAVEE
BoIL-32    MCFAKGVPYDQASLRSIMHKRVDDFCDKMGNEPE-EAQMEAALDETEEGLSEDICEFIED
Consensus  *---*-----*------------------*-------------------*----*---------

61
huIL-32β   YYEEQHPELTPLLEKERDGLRCRGNRSPV----PDVEDP----ATE--EPGESFCDKVMR
EqIL-32    HHQKNNSESAPLLPDVKPRLRRRAQKSSVLNPEPEGPGILQVEALEAPEPEESFWVRAWR
BoIL-32    HIQENLPES--LQESSPL-LQEARQGVRRRIQRPSV-----SARLEVQNPEESI----WA
Consensus  -------*---*--------*----------*------------*----*-**------*-

121
huIL-32β   WFQAMLQR-L-QTWWHGVLAWVKEKVVA------LVHAVQALWKQFQS---FCCSLSELF
EqIL-32    SFMGMLQR-LKQRWQAVLA-WVREKVAAGWQA--LCSVAQSINSVLES---FCSYMAGLF
BoIL-32    RALGRFQVIL-QSLQQRC--WDALTWLREKAVTFLEAICSVVKAVLGVLTDFCSSVGQLF
Consensus  ------*--*-*--------*----------*-----------------**-----**

181
huIL-32β   MSSF---QSYGAPRGDKEELTPQKCSEPQSSK
EqIL-32    RYH---IQV-----------------------
BoIL-32    ---GNLIQV-----------------------
Consensus  -------*------------------------
```

Fig. 4

A
0  5  15 30 45 60 90 120
IκB 
Actin 
B
0  5  15 30 45 60 90 120
Ⓟ-p38 MAPK 
p38 MAPK 
Fig. 11

A
EqIL-32 alpha (SEQ ID NO:18)
MGYPKTSREDNERWKIRFHSTLDRWLDDIEVQSQGEEQVCQCAPTPCSRNLGGRVVTMTMRRKNVPPQVD
LGPLTSPFSQRTFRSDLCHLPTLDLSLTTSLTSLLCTAWPPCPPCTSCSGFLLQV

B
EqIL-32 alpha (SEQ ID NO:19)
GCACGAGCTCGTGCCGTGTGCTGAGAGGCCCTTGGGGCAGGCACAGCCCCTGGAATCCTGAGCTGCCATG
GGCTACCCCAAGACGTCCAGAGAAGACAATGAACGTTGGAAGATCCGATTTCACAGCACTTTAGACCGGT
GGCTTGATGATATCGAAGTTCAATCCCAAGGAGAGGAACAGGTGTGTCAGTGTGCTCCCACGCCCTGCTC
CCGTAACCTCGGGGGTCGGGTGGTCACGATGACGATGAGGAGGAAGAACGTGCCACCTCAGGTCGATTTA
GGCCCTTTGACGTCCCCCTTTTCACAGAGAACCTTCAGAAGTGACCTTTGCCACCTGCCTACCCTTGACC
TGTCCTTGACCACCTCCCTCACCTCCTTGCTGTGCACAGCCTGGCCACCCTGCCCACCATGCACTTCCTG
CTCAGGTTTCCTTCTGCAGGTCTGACTTGTGGCTCCAGCGCATATGTCTTAATAAAGTTGTG

C
EqIL-32 beta (SEQ ID NO:16)
MGYPKTSREDNERWKIRFHSTLDRWLDDIEVQSQGEEQVDLGLEDLEEKFSENILDAVEEHHQKNNSESA
PLLPDVKPRLRRRAQKSSVLNPEPEGPGILQVEALEAPEPEESFWVRAWRSFMGMLQRLKQRWQAVLAWV
REKVAAGWQALCSVAQSINSVLESPCSYMAGLFRYHIQV

D
EqIL-32 beta (SEQ ID NO:20)
CTGAGAGGCCCTTGGGGCAGGCACAGCCCCTGGAATCCTGAGCTGCCATGGGCTACCCCAAGACGTCCAG
AGAAGACAATGAACGTTGGAAGATCCGATTTCACAGCACTTTAGACCGGTGGCTTGATGATATCGAAGTT
CAATCCCAAGGAGAGGAACAGGTCGATTTAGGCCTAGAAGACCTGGAGGAAAAATTCAGTGAAAACATTC
TTGACGCCGTGGAGGAGCACCATCAGAAGAACAACTCAGAATCTGCGCCTTTACTTCCTGACGTGAAGCC
CAGGTTACGTCGCAGAGCTCAGAAGTCCTCTGTCCTCAACCCTGAACCTGAGGGTCCAGGGATCCTGCAA
GTTGAGGCTCTAGAGGCACCCGAGCCTGAAGAAAGCTTTTGGGTCAGAGCATGGAGGTCGTTCATGGGA
TGCTACAGCGACTGAAGCAGAGGTGGCAGGCTGTACTGGCCTGGGTGCGAGAGAAGGTGGCTGCTGGCTG
GCAGGCCCTATGCAGTGTGGCCCAGTCCATTAATAGTGTGCTTGAGAGTTTCTGCTCCTATATGGCTGGG
TTGTTTAGGTACCACATCCAGGTCTAGGGGGCCCCATGGGGTCCAGGAGGGGTAGCCACACCTTGCAGCC
CTTTGACGTCCCCCTTTTCACAGAGAACCTTCAGAAGTGACCTTTGCCACCTGCCTACCCTTGACCTGTC
CTTGACCACCTCCCTCACCTCCTTGCTGTGCACAGCCTGGCCACCCTGCCCACCATGCACTTCCTGCTCA
GGTTTCCTTCTGCAGGTCTGACTTGTGGCTCCAGCGCATAGTCTT

Fig. 12

A
BoIL-32 beta (SEQ ID NO:17)
MCFAKGVPYDQASLRSIMHKRVDDFCDKMGNEPEEAQMEAALDETEEGLSEDICEFIEDHIQENLPESLQ
ESSPLLQEARQGVRRRIQRPSVSARLEVQNPEESIWARALGRFQVILQSLQQRCWDALTWLREKAVTFLE
AICSVVKAVLGVLTDFCSSVGQLFGNLIQV B
BoIL-32 beta (SEQ ID NO:21)
CGGATTCCCGGGATGCTCAGCTGGAGCTCTGGCTGCAGGATCTCAGGTCCCTTCGGGAGGACCCTAAGCC
ACCATGTGCTTCGCTAAGGGAGTCCCATATGACCAGGCTTCTCTGAGGTCCATAATGCACAAACGGGTGG
ATGATTTCTGTGATAAGATGGGAAATGAACCAGAAGAAGCACAGATGGAGGCAGCCCTAGATGAGACGGA
GGAGGGACTCAGCGAGGACATCTGTGAATTCATAGAAGATCACATTCAAGAGAACCTTCCCGAATCCCTG
CAGGAGTCCAGTCCCTTGCTTCAGGAAGCACGGCAAGGAGTACGCCGCAGAATCCAGAGACCTTCAGTCT
CTGCCCGTCTGGAGGTCCAGAATCCGGAAGAGAGCATCTGGGCCAGAGCCCTGGGGAGGTTCCAAGTAAT
TCTGCAGAGTCTCCAGCAGCGGTGTTGGGATGCGCTCACCTGGCTGCGGGAGAAGGCGGTGACCTTCCTG
GAGGCCATCTGCAGTGTGGTGAAGGCCGTCTTGGGAGTGCTGACGGATTTCTGCTCCTCTGTGGGGCAGC
TCTTCGGAAACCTCATCCAGGTCTAGGAGCCGCAGGTGGTTCTGGAGGAACTCCTCCTCATCTAGGAGGC
CCTGCACCATCCCCTTCCCAGAAACCATCTTGTGAAGCGACCTTTGCACTCCTGCTCACCCTTGACCCAT
CCTTTAACTGCCCTCACCTCCTGT C
BoIL-32 gamma (SEQ ID NO:22)
MCFTKRDPRVLASFRVLMVRSSFPRIAGVREAWVLLGEAENILAHLGPSREKNRDSFTQVHLCSQHNLVD
EFFDTMENEPEGAQMEAVLAETKEKFIKDAFKVMDNHIQENSPETLKESSPLLQEARQEVRCRIQRRSVS
TSLEVQNPEESIWARALRQFLGILQSFLSGCRDALTWLWEKAAACLQAICSAVEALWEVLTDFCSFVGQL
LCRSLIQV D
BoIL-32 gamma (SEQ ID NO:23)
CGGGATCTCAGCTGGAGCTCTGGCTGCAGGATCTCAGGTCCCAGCGGCAGGACCCTAAGCCACCATGTGC
TTCACTAAGAGAGACCCACGTGTCCTGGCTTCTTTCAGGGTGTTAATGGTAAGAAGCTCATTTCCACGTA
TAGCTGGGGTTCGGGAGGCCTGGGTTCTGCTGGGTGAAGCTGAGAACATTCTGGCCCACTTGGGACCCAG
CAGGGAGAAGAACCGAGATTCTTTTACTCAAGTCCATCTCTGTTCACAGCACAACCTTGTAGATGAATTT
TTCGATACAATGGAAAATGAACCAGAAGGAGCACAGATGGAGGCAGTCCTAGCAGAGACTAAGGAGAAAT
TCATCAAGGACGCCTTTAAAGTCATGGATAATCACATTCAAGAGAACAGTCCCGAAACCCTGAAGGAGTC
CAGTCCCTTGCTTCAGGAAGCACGGCAAGAAGTACGCTGCAGAATCCAGAGACGCTCCGTCTCCACCTCT
CTGGAGGTCCAGAATCCGGAAGAGAGCATCTGGGCCAGAGCCCTGCGGCAGTTCTTGGGCATTCTGCAGA
GTTTCCTGTCCGGGTGTCGGGATGCGCTCACCTGGCTGTGGGAGAAGGCCGCGGCCTGCCTACAGGCCAT
CTGCAGTGCGGTGGAGGCCCTCTGGGAAGTGCTCACGGATTTCTGCTCCTTTGTTGGGCAGCTCTTATGC
AGAAGCCTCATCCAGGTCTAAGAGCCTCACATGGTTCTGGAGGAGCCCCACCTCATTCAGAAGGCCCTGT
ACGATGCCCTTCCCGGAAACCATCTTCTGAAGCGACCTTTACCCTCCTGCTCACCCTTGACCCATCCTTT
AACTGCCCTCCCCTCCTGTCCTG

Fig. 13

A
OvIL-32 alpha (SEQ ID NO:24)
MCFARGVPHDQASLRSMLHTWVDHVCDKMGNEPEEAQMEAALAEMEEELSKDVCESWKITFKRTFPNPCR
SPVPCFRKRSKKYAAESRDPQSLPVWRTRNRKRASGPEPCGGSEVFCGVSGSGVAMY

B
OvIL-32 alpha (SEQ IDO:25)
CTGCGGTACCGGTCCGGATTCCCGGGCGAGACAGTGCTCAGCTGGAGCTCTGGCTGCAGGATCTCAGATC
CCAGCCGGAGGACCCTAATCCACCATGTGCTTCGCTAGGGGAGTCCCACATGACCAGGCTTCTCTGAGGA
GCATGCTGCACACCTGGGTGGATCATGTCTGTGATAAGATGGGAAATGAACCAGAAGAAGCACAGATGGA
GGCAGCCCTAGCAGAGATGGAGGAGGAACTCAGCAAGGATGTCTGTGAATCATGGAAGATCACATTCAAG
AGAACCTTCCCGAATCCCTGCAGGAGTCCAGTCCCTTGCTTCAGGAAGCGCAGCAAGAAGTACGCCGCAG
AATCCAGAGACCCTCAGTCTCTGCCTGTCTGGAGGACCAGAAACCGGAAGAGAGCATCTGGGCCAGAGCC
CTGCGGCGGTTCCGAGGTTTTCTGCGGAGTCTCTGGCAGCGGTGTTGCGATGTACTGACCTGGCTGCAGG
AGAAGGCGGCGGCCTGCCTGGAGGCCGTCTGCAGTGCGGTGAAGACCATCTGGGGAGTGCTGACGGATTT
CTGCTCCTCTGTGGGGCAGCTCTTCAGAAACCTCATCCAGGTCTAGGAGCCCCAGGTCGTTCTTGAGGAA
CTGCTCCTCATCTAGAAGGCCCTGCACAATCCCCTTCCCAGAAACCATCTTCTGAAGCGACCTTTACCCT
CCTGTTCACCCTTCACCAATCCTTTAACTGCCCTCACCTCCTGTCTGCAGGGACGACACCACAACATCAA
GCCAGGTTTCCCTTCTCCAAGTCTGACCCGTCTGTCAGGGA

C
SwIL-32 alpha (SEQ ID NO:26)
MRGVSATRTLPKAGPQPRSGLGLPLPRRVPEPPPIPAESSPLLNEVRQGVRSRVRRPPGHNQPHYALAVR
EPRQSTFRRILELFEEMLKRLQQRWRGALAWVQERAAACFRGLCRALEAFWSLVQSFCSSMGHAFGSVIQ
V

D
SwIL-32 alpha (SEQ ID NO:27)
ATGACTTGGAGGGGAACTGAGCGGCCAGGCCCAGCCCCTGGGAAAAGTCCTGGGGTCTGTGGGGCTGTTG
GCAGGAAAGCAGCCTGTGTCCAAGGCGGGGCATGAGGGGGGTGTCTGCCACCAGGACTCTCCCAAAGGCA
GGGCCTCAGCCAAGGTCAGGACTGGGGCTGCCTCTCCCAGGCGGGTCCCTGAACCACCCCCATCCCTG
CAGAATCCAGTCCTCTGCTCAACGAAGTCCGGCAGGGAGTCCGTTCTAGAGTCCGAAGGCCTCCTGGCCA
CAACCAGCCACATTATGCGCTAGCGGTCCGGGAGCCCAGGCAGAGCACTTTCAGACGCATCCTTGAGCTG
TTTGAGGAAATGCTGAAGCGCCTGCAGCAGAGGTGGAGGGGTGCCCTGGCTTGGGTGCAGGAAAGGGCTG
CTGCCTGCTTCCGGGGCTTGTGCAGGGCCCTTGAAGCTTTCTGGAGCCTGGTGCAGAGTTTTGCTCCTC
CATGGGGCACGCCTTCGGGAGTGTCATCCAGGTCTAAGGTGCTCCAGGTGAAATAAGAGTTTCTAGAGCA
CAACCTCCCCCTGCCTTGGCTAAAAAGGCAGCTGTAAGCCTTT

Fig. 14

COMPOSITIONS FOR REGULATION OF TUMOR NECROSIS FACTOR-ALPHA

This invention was made in part with government support under grants AI-15614 and HL-68743, from the National Institutes Health. As such, the United States government has certain rights in the invention.

FIELD OF THE INVENTION

The present invention relates to compositions and methods relating to an interleukin-18-inducible cytokine termed tumor necrosis factor-alpha inducing factor (TAIF) or interleukin-32 (IL-32). In particular, the present invention provides compositions and methods for treating autoimmune diseases and cancer, in part by regulation of tumor necrosis factor-alpha expression.

BACKGROUND OF THE INVENTION

Rheumatoid arthritis (RA) is a common chronic inflammatory arthritis that affects about 1% of adults worldwide, with a female predominance and a peak onset in the fourth decade of life (See, Firestein, "Rheumatoid Arthritis," in *Scientific American Medicine*, 2000; and Cohen, "Systemic Autoimmunity," in Paul (ed.) *Fundamental Immunology*, Lippincott-Raven Publishers: Philadelphia, pp. 1067-1088, 1999). Intense inflammation occurs in synovial joints, with infiltration of the synovial membrane by mononuclear phagocytes, lymphocytes and neutrophils, causing significant joint pain. In addition, RA patients generally develop loss of cartilage and bone around joints, which leads to a loss of mobility.

Although the cause of RA has not been precisely defined, various characteristics of the disease are indicative of an autoimmune component to RA etiology. In particular, macrophage and fibroblast-derived cytokines are abundantly expressed in rheumatoid joints (Firestein et al., *J Immunol*, 144:3347, 1994). Tumor necrosis factor alpha (TNFα) and interleukin-1 (IL-1) appear to be the major pathogenic factors, in that both can induce synoviocyte proliferation, collagenase production, and prostaglandin release, while overexpression can induce arthritis in animal models (Firestein, supra, 2000). IL-18 is also present in RA joints and can directly activate macrophages to produce proinflammatory cytokines (Gracie et al., *J Clin Invest*, 104:1393, 1999).

Current RA therapies are directed to analgesia, control of inflammation, and alteration of the disease course. More aggressive treatment approaches are now frequently adopted, with RA patients rapidly requiring a switch from non-steroidal anti-inflammatory drugs (NSAIDs) to a second line reagent such as methotrexate. Unfortunately, methotrexate alone does not adequately control RA in most patients, causing physicians to select either add-on therapy or a series of single agents (Firestein, supra, 2000), for example leflunomide, sulfasalazine, or a TNF inhibitor. TNF-inhibitors that have been used with some success to treat RA include TNF-reactive monoclonal antibodies (infliximab/REMICADE and adalimumab/HUMIRA) and a soluble TNF-receptor/immunoglobulin fusion protein (etanercept/ENBREL). However, it is desirable to provide clinicians with additional therapies to use alone or as cocktails to halt the progression of this debilitating disease.

SUMMARY OF TH INVENTION

The present invention relates to compositions and methods relating to an interleukin-18-inducible cytokine termed tumor necrosis factor-alpha inducing factor (TAIF) or interleukin-32 (IL-32). In particular, the present invention provides compositions and methods for treating autoimmune diseases and cancer, in part by regulation of tumor necrosis factor-alpha expression.

The present invention provides purified nucleic acids comprising a sequence at least 80% identical to SEQ ID NO:15, wherein the sequence encodes interleukin-32 (IL-32), and wherein the sequence comprises exon 3 and exon 4 of IL-32 in substantially contiguous association. In some preferred embodiments, the IL-32 is: an alpha isoform comprising the amino acid sequence set forth as SEQ ID NO:7; a beta isoform comprising the amino acid sequence set forth as SEQ ID NO:8; or a delta isoform comprising the amino acid sequence set forth as SEQ ID NO:10. In other embodiments, the sequence lacks intron 4 of IL-32, while in particularly preferred embodiments, the sequence is at least 90% identical to SEQ ID NO:15. Also provided are purified nucleic acids, comprising a sequence selected from the group consisting of SEQ ID NO:3, SEQ ID NO:4 and SEQ ID NO:6. In some embodiments, the sequence is operably linked to a heterologous promoter. In preferred embodiments, the nucleic acid is contained within a vector. Moreover, host cells comprising the vector are provided.

In addition, the present invention provides purified proteins encoded by nucleic acids comprising a sequence at least 80% identical to SEQ ID NO:15, wherein the sequence encodes interleukin-32 (IL-32), and wherein the sequence comprises exon 3 and exon 4 of IL-32 in substantially contiguous association. In some preferred embodiments, the IL-32 is: an alpha isoform comprising the amino acid sequence set forth as SEQ ID NO:7; a beta isoform comprising the amino acid sequence set forth as SEQ ID NO:8; or a delta isoform comprising the amino acid sequence set forth as SEQ ID NO:10. In other embodiments, the IL-32 is not a gamma isoform, while in preferred embodiments, the IL-32 does not comprise the amino acid sequence set forth as SEQ ID NO:14. In some preferred embodiments, the IL-32 is a recombinant protein expressed in a cell selected from the group consisting of a bacterial cell, a yeast cell, an insect cell, and a mammalian cell. In a subset of these embodiments, the recombinant protein is a fusion protein.

Also provided by the present invention are antibodies, which bind to IL-32. In some preferred embodiments the antibody is a monoclonal antibody, while in other embodiments, a Fab fragment of the monoclonal antibody is provided. In some embodiments, the monoclonal antibody (mAb) is chosen from but not limited to 32-4 and 32-9. Hybridoma cells that produce the 32-4 mAb are being deposited with the American Type Culture Collection (ATCC), 10801 University Boulevard, Manassas, Va. 20110-2209. Likewise, hybridoma cells that produce the 32-9 mAb are being deposited with ATCC. Additionally, in some preferred embodiments, the monoclonal antibody is chosen from but not limited to a chimeric monoclonal antibody, a humanized monoclonal antibody, and a human monoclonal antibody. In a subset of embodiments, the monoclonal antibody inhibits IL-32-induced TNFα production by a target cell, inhibits IL-32-induced IκB degradation in a target cell, and/or inhibits rapid IL-32-induced p38 MAPK phosphorylation in a target cell.

Moreover, the present invention provides methods for inducing TNFα production, comprising contacting at least one cell with an IL-32 protein under conditions suitable for inducing TNFα production. In preferred embodiments, the IL-32 protein is selected from the group consisting of an alpha isoform, a beta isoform, a gamma isoform and a delta isoform. In some embodiments the at least one cell comprises a leukocyte, while in a subset of these embodiments, the leukocyte is selected from the group consisting of monocytes and macrophages.

Also provided by the present invention are methods of treating a subject, comprising: providing a subject and an antibody that binds IL-32; and administering the antibody to the subject. In preferred embodiments, the IL-32 is selected from the group consisting of an alpha isoform, a beta isoform, a gamma isoform and a delta isoform. In particularly preferred embodiments, the subject has, is suspected of having, or is at risk of having an autoimmune disease. In some embodiments, the autoimmune disease is chosen from but not limited to multiple sclerosis, myasthenia gravis, autoimmune neuropathy, autoimmune uveitis, Crohn's disease, ulcerative colitis, primary biliary cirrhosis, autoimmune hepatitis, autoimmune hemolytic anemia, pernicious anemia, autoimmune thrombocytopenia, type 1 diabetes mellitus, Grave's disease, Hashimoto's thyroiditis, autoimmune oophoritis and orchitis, temporal arteritis, anti-phospholipid syndrome, Vasculitides, Behcet's disease, rheumatoid arthritis, systemic lupus erythematosus, scleroderma, polymyositis, dermatomyositis, spondyloarthropathy, Sjogren's syndrome, psoriasis, dermatitis herpetiformis, pemphigus vulgaris, and vitiligo. The present invention provides antibodies chosen from but not limited to a human monoclonal antibody and a humanized mouse monoclonal antibody. In preferred embodiments, the administering is done under conditions suitable for alleviating at least one symptom of an autoimmune disease.

Furthermore, the present invention provides methods for screening for inhibitors of IL-32, comprising: providing an IL-32 protein, and at least one drug candidate; and analyzing the effect of the drug candidate on at least one activity of the IL-32 protein. In some embodiments, the IL-32 protein is a recombinant protein selected from the group consisting of an alpha isoform, a beta isoform, a gamma isoform and a delta isoform. In preferred embodiments, the drug candidate is chosen from but not limited to an IL-32-reactive monoclonal antibody, and a dominant-negative IL-32 variant. In particularly preferred embodiments, the at least one activity of the IL-32 protein comprises upregulation of TNFα expression.

Also provided by the present invention are methods of treating a subject, comprising: providing a subject and an IL-32 protein; and administering the IL-32 protein to the subject. In preferred embodiments, the IL-32 protein is a recombinant protein selected from the group consisting of an alpha isoform, a beta isoform, a gamma isoform and a delta isoform. In particularly preferred embodiments, the subject has, is suspected of having, or is at risk of having cancer.

The present invention also provides methods and kits for measuring IL-32 concentration in sera of a subject comprising providing sera from a subject and a IL-32-reactive antibody, and screening the sera with the antibody under conditions suitable for quantifying IL-32. In some embodiments, the subject is an autoimmune disease patient, while in other embodiments, the subject is a sepsis patient. In some preferred embodiments, the screening is accomplished by electrochemiluminescence assay, while in other embodiments, the screening is accomplished by enzyme-linked immunosorbent assay. The IL-32-reactive antibody, in some embodiments, is chosen from but not limited to a polyclonal rabbit and human-IL-32 antibody, and a monoclonal mouse anti-human IL-32 antibody.

DESCRIPTION OF THE FIGURES

FIG. 2 graphically depicts the induction of TNFα expression upon treatment of mouse Raw 264.7 macrophage cells with recombinant IL-32α (TAIF) in the presence of polymyxin B. Panel A shows that the level of recombinant IL-32α in ion exchange chromatography fractions correlated with the levels of TNFα secreted by treated cells. Each ion exchange chromatograph fraction is shown after 10% SDS-PAGE followed by Coomassie blue staining. Panel B shows that recombinant IL-32α expressed in bacteria induced TNFα expression in a dose-dependent manner. Panel C shows that recombinant IL-32α expressed in mammalian cells also induced expression of TNFα. The amount of recombinant IL-32α was estimated by immunoblot.

FIG. 3 provides an alignment of the DNA sequences of the open reading frames of the four IL-32 splice variants (IL-32α disclosed as SEQ ID NO:3, IL-32β disclosed as SEQ ID NO:4, IL-32γ disclosed as SEQ ID NO:5, and IL-32δ disclosed as SEQ ID NO:6). The alignment was done with the ClustalW program (available on the web site of the Swiss node of EMBnet) and manually corrected. Myr and Gly indicate potential N-myristoylation or N-glycosylation sites, respectively.

FIG. 4 provides an alignment of the four human IL-32 splice variants in panel A (IL-32α disclosed as SEQ ID NO:7, IL-32β disclosed as SEQ ID NO:8, IL-32γ disclosed as SEQ ID NO:9, and IL-32δ disclosed as SEQ ID NO:10), as well as an alignment of IL-32β protein sequences from several mammalian species (human sequence disclosed as SEQ ID NO:8, equine disclosed as SEQ ID NO:16, and bovine disclosed as SEQ ID NO:17). The alignment was done with programs available on the web site of the Swiss node of EMBnet, and manually corrected.

FIG. 11 depicts IL-32α-induced IκB degradation (panel A), and p38 MAPK phosphorylation (panel B), after IL-32α (20 U/ml) treatment of mouse Raw 264.7 macrophage cells. For normalization purposes, the membrane was probed with goat anti-actin or rabbit anti-p38 MAPK.

FIG. 12 provides amino acid sequences of equine IL-32α (SEQ ID NO:18) and IL-32β (SEQ ID NO:16) in panels A and C respectively, as well as cDNA sequences of equine IL-32α (SEQ ID NO:19) and IL-32β (SEQ ID NO:20) in panels B and D, respectively.

FIG. 13 provides amino acid sequences of bovine IL-32β (SEQ ID NO:17) and IL-32γ (SEQ ID NO:22) in panels A and C respectively, as well as cDNA sequences of bovine IL-32β (SEQ ID NO:21) and IL-32γ (SEQ ID NO:23) in panels B and D, respectively.

FIG. 14 provides the amino acid (SEQ ID NO:24) and cDNA (SEQ ID NO:25) sequences of ovine IL-32α in panels A and B respectively. Also provided are the amino acid (SEQ ID NO:26) and cDNA (SEQ ID NO:27) sequences of swine IL-32α in panels C and D, respectively.

DEFINITIONS

Figure 1:
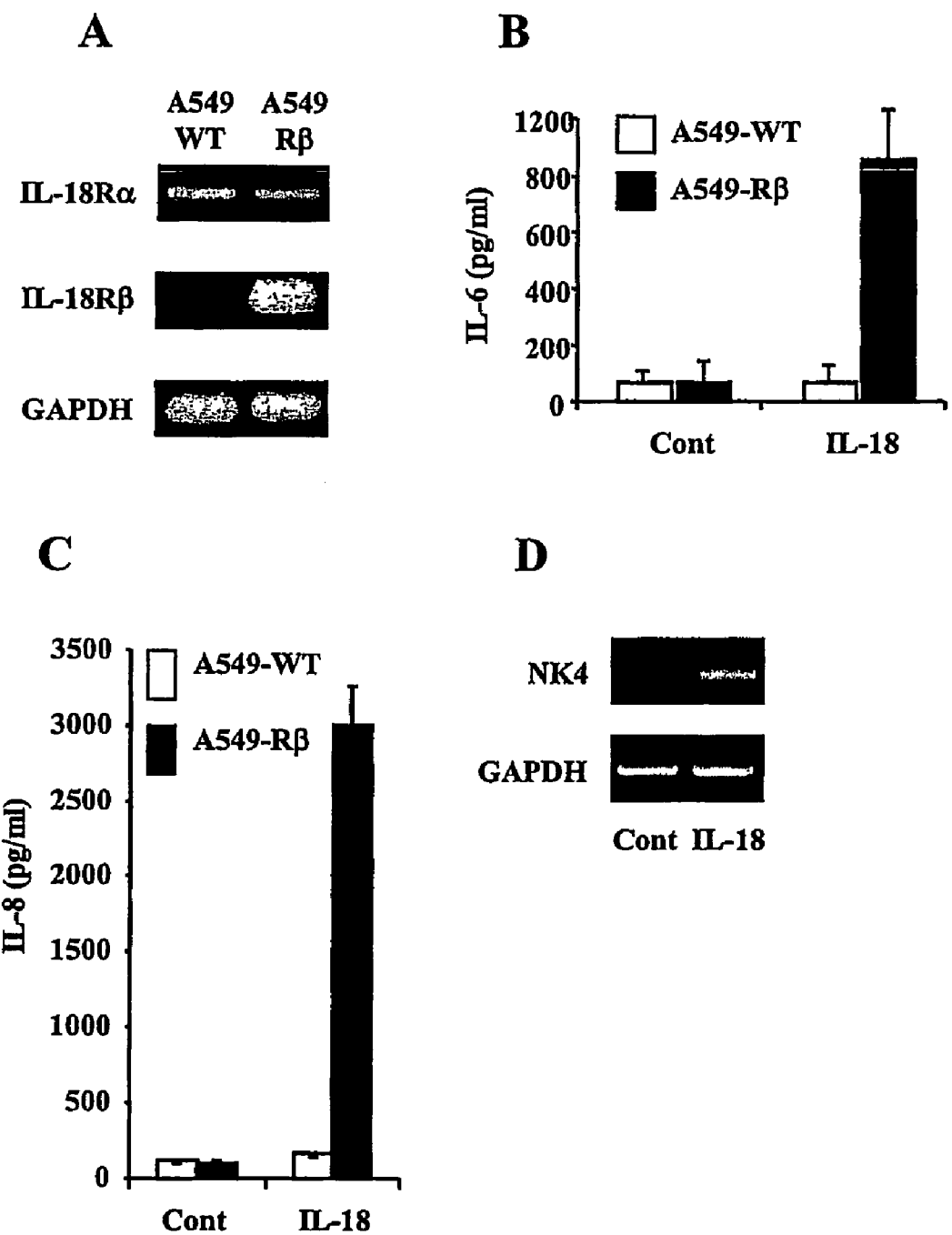
FIG. 1 shows the expression and activity of a functional IL-18Rβchain in human A549 lung carcinoma cells. Panel A provides the results of an RT-PCR analysis of IL-18Rβ expression in transfected and wild type A549 cells. Panels B and C provide graphs depicting IL-6 and IL-8 secretion respectively, in response to IL-18 (50 ng/ml) stimulation in transfected but not wild type A549 cells after 16 hours (N=7). Panel D shows the induction of NK4 (IL-32) RNA expression in transfected cells, in the presence and absence of IL-18.

To facilitate an understanding of the present invention, a number of terms and phrases are defined below:

The term "gene" refers to a nucleic acid (e.g., DNA) sequence that comprises coding sequences necessary for the production of a polypeptide or precursor or RNA (e.g., tRNA, siRNA, rRNA, etc.). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends, such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

In particular, the terms "TAIF gene" and "IL-32 gene" refers to the full-length IL-32 nucleotide sequence. However, it is also intended that the term encompass fragments of the IL-32 nucleotide sequence, as well as other domains (e.g., functional domains) within the full-length IL-32 nucleotide sequence. Furthermore, the terms "IL-32 gene," "IL-32 nucleotide sequence," and "IL-32 polynucleotide sequence" encompass DNA, cDNA, and RNA sequences.

The term "plasmid" as used herein, refers to a small, independently replicating, piece of DNA. Similarly, the term "naked plasmid" refers to plasmid DNA devoid of extraneous material typically used to affect transfection. As used herein, a "naked plasmid" refers to a plasmid substantially free of calcium-phosphate, DEAE-dextran, liposomes, and/or polyamines.

As used herein, the term "purified" refers to molecules (polynucleotides or polypeptides) that are removed from their natural environment, isolated or separated. "Substantially purified" molecules are at least 50% free, preferably at least 75% free, and more preferably at least 90% free from other components with which they are naturally associated.

The term "recombinant DNA" refers to a DNA molecule that is comprised of segments of DNA joined together by means of molecular biology techniques. Similarly, the term "recombinant protein" refers to a protein molecule that is expressed from recombinant DNA.

The term "fusion protein" as used herein refers to a protein formed by expression of a hybrid gene made by combining two gene sequences. Typically this is accomplished by cloning a cDNA into an expression vector in frame with an existing gene. The fusion partner may act as a reporter (e.g., βgal), may provide a tool for isolation purposes (e.g., GST) or may increase the half-life of the protein in vivo (e.g., IgG Fc).

Suitable systems for production of recombinant proteins include but are not limited to prokaryotic (e.g., *Escherichia coli*), yeast (e.g., *Saccaromyces cerevisiae*), insect (e.g., baculovirus), mammalian (e.g., Chinese hamster ovary), plant (e.g., safflower), and cell-free systems (e.g., rabbit reticulocyte).

As used herein, the term "coding region" refers to the nucleotide sequences that encode the amino acid sequences found in the nascent polypeptide as a result of translation of an mRNA molecule. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

Where amino acid sequence is recited herein in reference to a naturally occurring protein molecule, the term "amino acid sequence" and like terms such as "polypeptide" or "protein" are not meant to limit the amino acid sequence to the complete, native amino acid sequence associated with the recited protein molecule.

The term "wild-type" refers to a gene or gene product that has the characteristics of that gene or gene product when isolated from a naturally occurring source. A wild type gene is that which is most frequently observed in a population and is thus arbitrarily designed the "normal" or "wild-type" form of the gene.

As used herein, the terms "mutant," "polymorphism," and "variant," in reference to a gene or gene product, refer to alterations in sequence and/or functional properties (i.e., different characteristics) when compared to the wild-type gene or parental gene product. In some preferred embodiments, the term mutant refers to a gene or gene product that differs from a parental gene or gene product as a result of mutation. It is noted that naturally occurring and induced mutants can be isolated; these are identified by the fact that they have altered characteristics when compared to the wild-type gene or parental gene product. In addition, mutant genes can be artificially (e.g., site-directed mutagenesis) or synthetically produced in the laboratory.

The terms "interleukine-32," "IL-32," "TAIF," "tumor necrosis factor-alpha inducing factor," "NK4," and "natural killer cell transcript 4," as used herein refer to a human IL-32 gene (e.g., *Homo sapiens*—SEQ ID NO:11), and its gene products (e.g., wild type alpha, beta, gamma and delta isoforms, and variants thereof). IL-32 variants that differ from the wild type IL-32 sequences in fewer than 20% of the residues (preferably 10% or fewer, more preferably 5% or fewer and most preferably 1% or fewer), are also suitable for use in the methods and compositions of the present invention (this includes but is not limited to the gene product corresponding to the murine cDNA fragment disclosed as SEQ ID NO:12). In contrast, the terms NK4, TAIF and IL-32 as used herein, do not refer to the internal fragment of the hepatocyte growth factor (HGF), designated as HGF/NK4 (or also simply NK4, for N-terminal hairpin domain and subsequent four-kringle domains), which is a specific antagonist of HGF (Date et al., *FEBS Lett*, 420:1-6, 1997).

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, "Quantitative Filter Hybridization," in *Nucleic Acid Hybridization*. 1985). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

The terms "high stringency conditions" and "stringent conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

As used herein, the term "Northern blot" refers to methods for transferring denatured RNA onto a solid support for use in a subsequent hybridization assay. Total RNA or polyA-enriched RNA is typically electrophoresed in an agarose gel, transferred to a membrane and probed with a radioactively-labeled DNA or RNA fragment to detect specific RNA sequences. Northern blots are routinely used in the art (See, e.g., Thomas, *Proc Natl Acad Sci USA* 77:5201-5205, 1980; and Ausubel et al. (eds.), *Current Protocols in Molecular Biology*, John Wiley & Sons, Inc., New York, 1994).

The term "Southern blot," as used herein, refers to methods for transferring denatured DNA, which has been fractionated by agarose gel electrophoresis, onto a solid support, for use in a subsequent hybridization assay. These methods typically entail the digestion of genomic DNA with a suitable restriction enzyme prior to agarose gel electrophoresis, transfer of the DNA to a membrane and incubation with a radioactively-labeled DNA or RNA fragment for detection of specific DNA sequences. Southern blots are routinely used in the art (See, Southern, *J Mol Biol* 98:503-517, 1975; and Ausubel et al., supra, 1994).

As used herein, the term "polymerase chain reaction (PCR)" refers to a method for increasing the concentration of a segment of a target sequence in a DNA mixture without cloning or purification (See, e.g., U.S. Pat. Nos. 4,683,195, 4,683,202, and 4,965,188, hereby incorporated by reference). This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are the to be "PCR amplified." When the template is RNA, a reverse transcription (RT) step is completed prior to the amplification cycles. Thus, this variation is termed "RT-PCR."

The term "antibody" refers to polyclonal and monoclonal antibodies. Polyclonal antibodies which are formed in the animal as the result of an immunological reaction against a protein of interest or a fragment thereof, can then be readily isolated from the blood using well-known methods and purified by column chromatography, for example. Monoclonal antibodies can also be prepared using known methods (See, e.g., Winter and Milstein, *Nature,* 349, 293-299, 1991). As used herein, the term "antibody" encompasses recombinantly prepared, and modified antibodies and antigen-binding fragments thereof, such as chimeric antibodies, humanized antibodies, multifunctional antibodies, bispecific or oligo-specific antibodies, single-stranded antibodies and F(ab) or F(ab)$_2$ fragments. The term "reactive" in used in reference to an antibody indicates that the antibody is capable of binding an antigen of interest. For example, an IL-32-reactive antibody is an antibody that binds to IL-32 or to a fragment of IL-32.

The term "dominant-negative mutant" refers to molecules that lack wild type activity, but which effectively compete with wild type molecules for substrates, receptors, etc., and thereby inhibit the activity of the wild type molecule. In preferred embodiments, the term "IL-32 dominant negative mutant" refers to a IL-32 mutant protein which competes with the wild type IL-32 protein for IL-32 receptors, but which fails to induce downstream effects such as degradation of IκB, phosphorylation of p38 MAPK, and TNFα production. Suitable dominant-negative IL-32 variants may be selected from libraries of random IL-32 mutants or may be designed rationally, as has been described in the TNF system (Steed et al., *Science,* 301:1895-1898, 2003).

The term "portion" when used in reference to a nucleotide sequence refers to fragments of that sequence, which range in size from 10 nucleotides to the entire nucleotide sequence minus one nucleotide.

As used herein, the term "biologically active" refers to a molecule having structural, regulatory and or biochemical functions of a wild type IL-32 molecule. In some instances, the biologically active molecule is a homolog of a mammalian IL-32 molecule, while in other instances the biologically active molecule is a portion of a mammalian IL-32 molecule. Other biologically active molecules that find use in the compositions and methods of the present invention include but are not limited to mutant (e.g., variants with at least one deletion, insertion or substitution) mammalian IL-32 molecules. Biological activity is determined for example, by measuring TNFα-induction in vitro as described in the experimental examples.

As used herein the term "animal" refers to any member of the kingdom Animalia, which includes living things that have cells differing from plant cells with regard to the absence of a cell wall and chlorophyll and the capacity for spontaneous movement. Preferred embodiments of the present invention are primarily directed to vertebrate (backbone or notochord) members of the animal kingdom.

The terms "patient" and "subject" refer to a mammal (human or animal) that is a candidate for receiving medical treatment.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to animals that receive a mock treatment (e.g., PBS alone or normal rabbit IgG in saline).

The terms "sample" and "specimen" are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid, semen, saliva, and wound exudates, as well as solid tissue. However, these examples are not to be construed as limiting the sample types applicable to the present invention.

The term "leukocyte" as used herein, refers to cells called white blood cells that help the body fight infections and other diseases, and include for instance granulocytes (e.g., neutrophils, eosinophils, basophils), mononuclear phagocytes, and lymphocytes (e.g., B cells, T cells, natural killer cells).

As used herein, the term "monocyte" refers to a mononuclear phagocyte circulating in blood that will later emigrate into tissue and differentiate into a macrophage. The term "macrophage" refers to relatively long-lived phagocytic cells of mammalian tissues, derived from blood monocytes. Macrophages from different sites have distinctly different properties. Main types are peritoneal and alveolar macrophages, tissue macrophages (histiocytes), Kupffer cells of the liver and osteoclasts. Macrophages play an important role in killing some bacteria, protozoa and tumour cells, in releasing substances that stimulate other cells of the immune system, and presenting processed antigen to T lymphocytes.

The term "inflammation" as used herein, refers to the tissue response to trauma, characterized by increased blood flow and entry of leukocytes into the tissues, resulting in swelling, redness, elevated temperature and pain.

As used herein, the term "symptom" refers to any subjective evidence of disease or of a patient's condition (e.g., a change in a patients condition indicative of some bodily or mental state).

For instance, the phrase "symptoms of inflammation" in the context of inflammatory bowel disease (IBD) is herein defined to include, but is not limited to symptoms such abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g., anemia) or a test that detects the presence of blood (e.g., rectal bleeding).

Similarly, the phrase "under conditions such that the symptoms are reduced" in the context of IBD refers to any degree of qualitative or quantitative reduction in detectable symptoms of IBD, including but not limited to, a detectable impact on the rate of recovery from disease (e.g., rate of weight gain), or the reduction of at least one of the following symptoms: abdominal pain, diarrhea, rectal bleeding, weight loss, fever, loss of appetite, dehydration, anemia, distention, fibrosis, inflamed intestines and malnutrition.

The term "autoimmune disease" includes but is not limited to the following diseases: multiple sclerosis, myasthenia gravis, autoimmune neuropathies (such as Guillain-Barré), autoimmune uveitis, Crohn's disease, ulcerative colitis, primary biliary cirrhosis, autoimmune hepatitis, autoimmune hemolytic anemia, pernicious anemia, autoimmune thrombocytopenia, type 1 diabetes mellitus, Grave's disease, Hashimoto's thyroiditis, autoimmune oophoritis and orchitis, temporal arteritis, anti-phospholipid syndrome, Vasculitides (such as Wegener's granulomatosis), Behcet's disease, rheumatoid arthritis, systemic lupus erythematosus, scleroderma, polymyositis, dermatomyositis, spondyloarthropathies (such as ankylosing spondylitis), Sjogren's syndrome, psoriasis, dermatitis herpetiformis, pemphigus vulgaris, and vitiligo.

As used herein, the terms "rheumatoid arthritis" and "RA" refer to a chronic inflammatory disease in which there is destruction of joints. RA is considered to be an autoimmune disorder in which immune complexes are formed in joints and excite an inflammatory response (complex mediated hypersensitivity). Cell-mediated (type IV) hypersensitivity also occurs, resulting in the accumulation of macrophages and leading to the destruction of the synovial lining.

The terms "IBD" and "inflammatory bowel disease," as used herein, are general terms that encompass several disease processes, most commonly, ulcerative colitis and Crohn's disease.

As used herein, the term "Crohn's disease" refers to an inflammatory disease of the gastrointestinal tract. Common symptoms include recurrent abdominal pains, fever, nausea, vomiting, weight loss, and diarrhea that is occasionally bloody.

The terms "compound" and "drug candidate" refers to any chemical or biological entity (e.g., including pharmaceuticals, drugs, and the like) that can be used to treat or prevent a disease, illness, sickness, or disorder of bodily function. Compounds comprise both known and potential therapeutic compounds. A compound can be determined to be therapeutic by screening, e.g., using the screening methods of the present invention. A "known therapeutic compound" refers to a therapeutic compound that has been shown (e.g., through animal trials or prior experience with administration to humans) to be effective in such treatment or prevention.

As used herein, the term "agonist" refers to molecules or compounds that mimic the action of a "native" or "natural" compound. Agonists may be homologous to these natural compounds in respect to conformation, charge or other characteristics. Thus, agonists may be recognized by receptors expressed on cell surfaces. This recognition may result in physiologic and/or biochemical changes within the cell, such that the cell reacts to the presence of the agonist in the same manner as if the natural compound was present. Agonists may include proteins, nucleic acids, carbohydrates, or any other molecules that bind or interact with IL-32 binding protein(s).

As used herein, the terms "antagonist" and "inhibitor" refer to molecules or compounds that inhibit the action of a "native" or "natural" compound. Antagonists may or may not be homologous to these natural compounds in respect to conformation, charge or other characteristics. Thus, antagonists may be recognized by the same or different receptors that are recognized by an agonist. Antagonists may have allosteric effects, which prevent the action of an agonist (e.g., prevent native IL-32 from binding to IL-32 receptors). In contrast to the agonists, antagonistic compounds do not result in physiologic and/or biochemical changes within the cell such that the cell reacts to the presence of the antagonist in the same manner as if the natural compound was present. Antagonists and inhibitors may include proteins, nucleic acids, carbohydrates, or any other molecules that bind or interact with IL-32 binding proteins or which prevent formation of functional IL-32 multimers.

As used herein, the term modulate, refers to a change or an alteration in biological activity. Modulation may be an increase or a decrease in protein activity, a change in binding characteristics, or any other change in the biological, functional, or immunological properties associated with the activity of a protein or other structure of interest.

DESCRIPTION OF THE INVENTION

Interleukin-18 (IL-18) is multifunctional cytokine having roles in both the innate and adapted immune responses. IL-18 has been studied for its effect in the broad spectrum of Th1 or Th2 related autoimmune diseases (Okamura et al., *Nature*, 378:88-91, 1995, Nakanishi et al., *Cytokine Growth Factor Rev*, 12:53-72, 2001; and Okamura et al., *Adv Immunol*, 70:281-312, 1998). IL-1 and IL-18 belong to the IL-1 family, which share structural similarity, require caspase-1 for processing (Bazan et al., *Nature*, 379:591, 1996; and Gu et al., *Science*, 275:206-209, 1997). IL-18 also triggers similar signaling pathways including recruiting IL-1 receptor-associated kinases (IRAKs), the formation of IRAK complexes with the tumor necrosis factor (TNF) receptor-associated factor-6, and activation of the cascade of IκBα/NF-κB (Kojima et al., *Biochem Biophy Res Commun*, 244:183-186, 1998; Matsumoto et al., *Biochem Biophys Res Commun*, 234:454-457, 1997; and Robinson et al., *Immunity*, 7:571-581, 1997). Members of the IL-1 cytokine family are thought to play pathological roles in autoimmune and inflammatory diseases, since blocking IL-1 and IL-18 activities reduces disease severity in subjects with rheumatoid arthritis and systemic inflammation (Arend, *Adv Immunol*, 54:167-227, 1993; Dinarello, *Blood*, 87:2095-2147, 1996; Novick et al., *Immunity*, 10:127-136, 1999; and Banda et al., *J Immunol*, 170: 2100-2105, 2003). However, there is an obstacle to studying IL-18-inducible genes, since only a few cell lines respond to IL-18, for example human NK and KG-1 cell lines. In addition, although these cell lines respond to IL-18, they require co-stimulatory factors, such as IL-2, IL-12, or IL-15, respectively, in order to manifest IL-18 responsiveness (Ahn et al., *J Immunol*, 159:2125-2131, 1997, Ohtsuki et al., *Anticancer Res*, 17:3253-3258, 1997; Lauwerys et al., *J Immunol*, 165:1847-1853, 2000; and Hoshino et al., *J Immunol*, 162:51-59, 1999). The requirement for a co-stimulatory factor prevents an independent assessment of IL-18 induction of gene expression.

IL-18 has two known receptor chains, a ligand binding IL-18Rα chain and a signal transducing IL-18R, chain. Both chains of the IL-18 receptor belong to the IL-1 receptor family and consist of three Ig-like domains in the extracellular region (Kato et al., *Nat Struct Biol*, 10:966-971, 2003; and Yamamoto et al., *Biochem Biophys Res Commun*, 317:181-186, 2004). An additional component involved in IL-18 regulation is the IL-18 binding protein (IL-18BP). IL-18BP is not a part of the IL-18 signaling complex but rather antagonizes IL-18 activity (Kim et al., *Proc Natl Acad Sci USA*, 97:1190-1195, 2000; and Novick et al., *Immunity*, 10:127-136, 1999). IL-18BP is a secreted receptor-like molecule consisting of a single Ig-like domain. IL-18BP shares significant homology with viral proteins, and neutralizes the biological activities of human IL-18 (Xiang and Moss, *Virology*, 257:297-302, 1999; Reading and Smith, *J Virol*, 77:9960-9968, 2003; Esteban and Buller, *Virology*, 323:197-207, 2004; and Esteban et al., *J Gen Virol*, 85:1291-1299, 2004).

In the absence of co-stimulants, non-immune cells do not respond to IL-18, due to little or no expression of the IL-18Rβ chain (Thomassen et al., *J Interferon Cytokine Res*, 18:1077-1088, 1998; and Chandrasekar et al., *Biochem Biophys Res Commun*, 303:1152-1158, 2003). Therefore, it was necessary to generate a stable clone expressing the IL-18Rβ chain, since this receptor component is required for transmitting an IL-18 signal (Thomassen et al., supra, 1998; and Kim et al., *J Immunol*, 166:148-154, 2001). Stable expression of the IL-18Rβ chain was accomplished in the human lung carcinoma A549 cell (A549-Rβ), which made these cells responsive to IL-18 even in the absence of co-stimulation. The stable A549-Rβ clone was used to identify IL-18 inducible genes by microarray analysis. The microarray study described in Example 1, revealed the IL-18 induction of a cytokine-like molecule that was described 12 years ago as natural killer cell transcript 4 or simply NK4 (Dahl et al., *J Immunol*, 148:597-603, 1992). It should be noted that the term NK4 is presently used to be described a variant of hepatocyte growth factor (Martin et al., *J Cell Physiol*, 192:268-275, 2002). There is no sequence homology between the hepatocyte growth factor variant and the NK4/IL-32 transcript. More recently, increased expression of NK4 has been reported in PBMC from patients receiving high-dose IL-12 therapy for malignant melanoma (Panelli et al., *Genome Biol*, 3(7):RESEARCH0035, 2002), but the function of NK4 has remained unknown until development of the present invention.

As is described in detail in the experimental examples, a novel inflammatory cytokine termed interleukin-32 (IL-32) or the tumor necrosis factor alpha-inducing factor (TAIF) has been identified through a microarray analysis of A549-Rβ cells. In addition, the gene structure, expression pattern, and function of IL-32 have been elucidated. Prior to development of the present invention, a single isoform of IL-32 (TAIFγ/NK4) had been described as a lymphocyte transcript of unknown function (Dahl et al., *J Immunol*, 148:597-603, 1992), which is transcribed from human chromosome 16p13.3 within or adjacent to the Familial Mediterranean fever locus (Bernot et al., *Genomics*, 50:147-160, 1998). As is shown herein, although IL-32 lacks sequence homology to the known cytokine families, it is clearly a cytokine by virtue of its ability to induce TNFα secretion and to signal through the classical pathways of known proinflammatory cytokines. Moreover, IL-32 is contemplated to be a member of the IL-1 cytokine family (Ghayur et al., *Nature*, 386:619-623, 1997; Cerretti et al., *Science*, 256:97-100, 1992, and Kuida et al., *Science*, 267:2000-2003, 1995), due to similarities in IL-32 regulation, and to the lack of a clear signal peptide. In addition, like IL-1 and IL-18, IL-32 is secreted primarily from stimulated cells. As demonstrated for the first time herein, IL-32 triggered typical proinflammatory cytokine signal pathways, NFκB and p38 MAPK, thereby inducing production of the proinflammatory cytokine, TNFα. Similarly, IL-1β, IL-18, and LPS induced IL-32 expression, and unlike the original description of NK4 in activated NK or T-cells, ubiquitous IL-32 expression was observed in various organs. The IL-32 expression pattern resembles that of IL-15, which is also produced by a wide variety of tissues. This is in contrast to IL-2, which is exclusively produced by activated T cells (Bamford et al., *Proc Natl Acad Sci USA*, 93:2897-2902, 1996; and Grabstein et al., *Science*, 264:965-968, 1994).

The induction of TNFα by IL-32 indicates that this cytokine has an important role in autoimmune/inflammatory disease pathology. The high level of IL-32 observed in the circulation of some patients with sepsis (as compared to that observed in the sera of healthy individuals) has also not been documented before development of the present invention. Thus, blocking IL-32 activity is contemplated to be a highly effective therapeutic approach in various autoimmune diseases, similar to successful TNFα blocking strategies (Davis et al., *Ann Rhem Dis*, 59Suppl1:i41-3, 2000; and Shanahan and St Clair, *Clin Immunol*, 103:231-242, 2002). It is also contemplated that IL-32-based compositions will find use in the treatment of cancer and in other diseases where induction of cell death or apoptosis comprising TNFα production is beneficial.

In addition, it is contemplated that the mouse Raw 264.7 macrophage cell line expresses an IL-32 receptor, which is activated when bound by IL-32 (extracellular IL-32 function). However, it is also contemplated that IL-32 has an intracellular function, since IL-32 was also detected in cell lysates. Thus, it is contemplated that IL-32 is active as both an intracellular and as an extracellular protein similar to IL-1α (Stevenson et al., *Proc Natl Acad Sci USA*, 94:508-513, 1997) and high mobility group-1 (Wang et al., *Science*, 285:248-251, 1999).

The secretion of IL-32 in the absence of a clear signal peptide is characteristic of several cytokine families (Cerretti et al., *Science*, 256:97-100, 1992; Kuida et al., *Science*, 267:2000-2003, 1995; and Ghayur et al., *Nature*, 386:619-623, 1997). Similar to IL-1β and IL-18, IL-32 is secreted as a soluble protein in cell culture media of stimulated primary cells, as well as cell lines. IL-32 does not possess potential caspase-1 cleavage sites by primary sequence analysis, and although new splice variants have been found, none possess a typical hydrophobic signal peptide at the N-terminus.

The existence of IL-32 in multiple species is evidence of an evolutionarily conserved molecule that is contemplated to play an important function in regulation of inflammation. Fewer IL-32 isoforms were identified in other mammalian species, although this result may reflect the relative lack of ESTs for these species. Similarly an extensive search for a mouse IL-32 homologue was unsuccessful. However, it is possible that the putative murine IL-32 gene has very low homology with the human gene, since equine and bovine IL-32 homologs share only 31.8-28.1% sequence identity with human IL-32.

Some preferred embodiments of the present invention are described in the following sections: (I) IL-32 Polynucleotides; (II) IL-32 Polypeptides; (III) IL-32 Antibodies; (IV) Pharmaceutical Compositions Comprising IL-32 Polynucleotides, Polypeptides or Antibodies; and (V) Methods for Identifying IL-32 Inhibitors.

I. IL 32 Polynucleotides

The present invention provides nucleic acids encoding IL-32 proteins, homologs, variants, and mutants (e.g., SEQ ID NOs: 3, 4, 6). In some embodiments, the present invention provides polynucleotide sequences that are capable of hybridizing to SEQ ID NOs: 3, 4, 6 under conditions high stringency, as long as the polynucleotide sequence capable of hybridizing encodes a protein that retains the TNFα-inducing activity of the naturally occurring IL-32 gene. In some embodiments, the protein that retains the TNFα-inducing activity of naturally occurring IL-32 is 80% homologous to wild-type IL-32, preferably 90% homologous to wild-type IL-32, more preferably 95%, and most preferably 99% homologous to wild-type IL-32. In particularly preferred embodiments, the protein that retains IL-32 biological activity comprises a nucleic acid sequence encoding the contiguous amino acid sequence LKARMHQAIERFYDKMQN-AESGRGQV (SEQ ID NO:13), and which is 99% homologous to wild-type IL-32 (IL-32α, IL-32β, IL32γ, IL-32δ). In some preferred embodiments, the nucleic acid sequence does not encode the amino acid sequence set forth in SEQ ID NO:14. In a subset of these embodiments, the nucleic acid sequence comprises the sequence set forth in SEQ ID NO:15 (exon 3 adjacent to exon 4). In preferred embodiments, hybridization conditions are based on the melting temperature ($T_m$) of the nucleic acid binding complex and confer a defined "stringency" as explained above in the definition section.

In other embodiments of the present invention, alleles of IL-32 are provided. In preferred embodiments, alleles result from a mutation, (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In still other embodiments of the present invention, the nucleotide sequences of the present invention may be engineered in order to alter a IL-32 coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

A modified peptide can be produced in which the nucleotide sequence encoding the polypeptide has been altered, such as by substitution, deletion, or addition. In some preferred embodiments, these modifications do not significantly the TNFα-inducing activity of the modified IL-32 (e.g., IL-32 agonists), while in other preferred embodiments, these modifications eliminate TNFα-inducing activity of the modified IL-32 (e.g., IL-32 antagonists). In other words, any given construct can be evaluated in order to determine whether it is a member of the genus of modified or variant IL-32's of the present invention as defined functionally, rather than structurally. In preferred embodiments, the activity of variant or mutant IL-32 is evaluated by the methods described in Example 2 (TNFαinduction).

Moreover, as described above, variant forms of IL-32 are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of IL-32 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry, pg.* 17-21, 2nd ed, WH Freeman and Co., 1981). Whether a change in the amino acid sequence of a peptide results in a functional homolog can be readily determined, by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

II. IL-32 Polypeptides

In other embodiments, the present invention provides IL-32 polynucleotide sequences that encode IL-32 polypeptide sequences. IL-32 polypeptides (e.g., SEQ ID NOs: 7, 8, 10) are described in FIG. 4. Other embodiments of the present invention provide fragments, fusion proteins or functional equivalents of these IL-32 proteins. In still other embodiment of the present invention, nucleic acid sequences corresponding to these various IL-32 homologs and mutants may be used to generate recombinant DNA molecules that direct the expression of the IL-32 homologs and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NOs: 3, 4 and 6, which encode substantially the same or a functionally equivalent amino acid sequence, may be used to clone and express IL-32.

A. Vectors for Production of IL-32

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 3, 4, 6). In some embodiments of the present invention, the constructs comprise a vector, such as a plasmid or viral vector, into which a sequence of the invention has been inserted, in a forward or reverse orientation. In still other embodiments, the heterologous structural sequence is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

B. Host Cells for Production of IL-32

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomnyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation. Alternatively, in some embodiments, the IL-32 polypeptides are produced using conventional peptide synthesizers.

C. Purification of IL-32

The present invention also provides methods for recovering and purifying IL-32 from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-re-folding steps can be used as necessary, in completing configuration of the mature protein. In still other embodiments of the present invention, high performance liquid chromatography (HPLC) can be employed for final purification steps.

The present invention further provides polynucleotides having the coding sequence fused in frame to a marker sequence, which allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used.

D. IL-32 Fusion Proteins

The present invention also provides fusion proteins incorporating all or part of IL-32. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of an IL-32 protein.

In addition to utilizing fusion proteins to enhance immunogenicity, it is widely appreciated that fusion proteins can also facilitate the expression of proteins, such as the IL-32 protein of the present invention. Accordingly, in some embodiments of the present invention, IL-32 can be generated as a glutathione-5-transferase (i.e., GST fusion protein). It is contemplated that such GST fusion proteins will enable easy purification of IL-32, such as by the use of glutathione-derivatized matrices. In another embodiment of the present invention, a fusion gene coding for a purification leader sequence, such as a poly-(His)/enterokinase cleavage site sequence at the N-terminus of the desired portion of IL-32, can allow purification of the expressed IL-32 fusion protein by affinity chromatography using a $Ni^{2+}$ metal resin. In still another embodiment of the present invention, the purification leader sequence can then be subsequently removed by treatment with enterokinase.

E. IL-32 Variants

Still other embodiments of the present invention provide mutant or variant forms of IL-32. It is possible to modify the structure of a peptide having an activity of IL-32 for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject IL-32 proteins as defined herein. A modified peptide can be produced in which the amino acid sequence has been altered, such as by amino acid substitution, deletion, or addition. In some embodiments, preferred IL-32 variants include IL-32 agonists (e.g., IL-32 variants that possess TNFα-inducing activity), while other preferred IL-32 variants include IL-32 antagonists (e.g., IL-32 variants that do not possess TNFα-inducing activity and that inhibit the TNFα-inducing activity of wild type IL-32 proteins).

III. IL 32 Antibodies

Antibodies can be generated to allow for the detection of IL-32 proteins. The antibodies may be prepared using various immunogens. In one embodiment, the immunogen is a human IL-32 peptide to generate antibodies that recognize human IL-32. Such antibodies include, but are not limited to polyclonal, monoclonal, chimeric, single chain, Fab fragments, and Fab expression libraries.

Various procedures known in the art may be used for the production of polyclonal antibodies directed against IL-32. For the production of antibody, various host animals can be immunized by injection with the peptide corresponding to the IL-32 epitope including but not limited to rabbits, mice, rats, sheep, goats, etc. In a preferred embodiment, the peptide is conjugated to an immunogenic carrier (e.g., diphtheria toxoid, bovine serum albumin, or keyhole limpet hemocyanin). Various adjuvants may be used to increase the immunological response, depending on the host species, including but not limited to Freund's (complete and incomplete), mineral gels (e.g., aluminum hydroxide), surface-active substances (e.g., lysolecithin, pluronic polyols, polyanions, peptides, oil emulsions, dinitrophenol, and potentially useful human adjuvants such as Bacille Calmette-Guerin).

For preparation of monoclonal antibodies directed toward IL-32, it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press*, Cold Spring Harbor, N.Y.). These include but are not limited to the hybridoma technique (Köhler and Milstein, *Nature* 256:495-497, 1975), as well as the trioma technique, the human B-cell hybridoma technique (See e.g., Kozbor et al., *Immunol Today,* 4:72, 1983), and the EBV-hybridoma technique to produce human monoclonal antibodies (Cole et al., in *Monoclonal Antibodies and Cancer Therapy*, Alan R— Liss, Inc., pp. 77-96, 1985).

In addition, it is contemplated that techniques described for the production of single chain antibodies (U.S. Pat. No. 4,946,778 herein incorporated by reference) will find use in producing IL-32 specific single chain antibodies. An additional embodiment of the invention utilizes the techniques described for the construction of Fab expression libraries (Huse et al., *Science,* 246:1275-1281, 1989) to allow rapid and easy identification of monoclonal Fab fragments with the desired specificity for IL-32.

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

The foregoing antibodies can be used in methods known in the art relating to the localization and structure of IL-32 (e.g., for Western blotting), measuring levels thereof in appropriate biological samples, etc. The antibodies can be used to detect IL32 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human IL-32 using an appropriate strategy (e.g., ELISA or radioimmunoassay) and format (e.g., microwells, dipstick etc.). Alternatively, proteins in the sample can be size separated (e.g., by polyacrylamide gel electrophoresis (PAGE), in the presence or not of sodium dodecyl sulfate (SDS), and the presence of IL-32 detected by immunoblotting (Western blotting). Immunoblotting techniques are generally more effective with antibodies generated against a peptide corresponding to an epitope of a protein, and hence, are particularly suited to the present invention.

Particularly preferred embodiments of the present invention comprise IL-32 antibodies for the treatment of autoimmune diseases such as rheumatoid arthritis. IL-32-reactive antibodies that neutralize the TNFα-inducing activity of IL-32 are contemplated relieve at least one RA disease symptom and in especially preferred embodiments are contemplated to slow RA disease progression. Additionally teaching related to the production and use of therapeutic antibodies, which is contemplated to be applicable to the IL-32 system, is found in U.S. Pat. No. 6,277,969 and U.S. Pat. No. 6,448,380 (both herein incorporated by reference) directed to therapeutic TNF-reactive antibodies.

IV. Pharmaceutical Compositions Comprising IL-32 Nucleic Acids, Peptides, or Antibodies The present invention further provides pharmaceutical compositions which may comprise all or portions of IL-32 polynucleotide sequences, IL-32 polypeptides, inhibitors or antagonists of IL-32 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating autoimmune diseases and cancer. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, IL-32 nucleotide and IL-32 amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, IL-32 polynucleotide sequences or IL-32 amino acid sequences may be administered alone to individuals subject to or suffering from a disease.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of IL-32 may be that amount that induces production of TNFα. Determination of effective amounts is well within the capability of those skilled in the art, especially in light of the disclosure provided herein.

For any compound used in the method of the invention, the therapeutically effective dose can be estimated initially from cell culture assays. Then, preferably, dosage can be formulated in animal models (particularly murine models) to achieve a desirable circulating concentration range that adjusts TNFα levels.

A therapeutically effective dose refers to that amount of IL-32, which ameliorates at least one symptom of the disease state (e.g., cancer) or to that amount of IL-32 antibody or antagonist, which ameliorates at least one symptom of a disease state (e.g., autoimmune disease such as rheumatoid arthritis). Toxicity and therapeutic efficacy of such compounds can be determined by standard pharmaceutical procedures in cell cultures or experimental animals ($LD_{50}$, the dose lethal to 50% of the population; and $ED_{50}$, the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration. Normal dosage amounts may vary from 0.1 to 100,000 micrograms, up to a total dose of about 1 g, depending upon the route of administration.

V. Drug Screening Using IL32

The present invention provides methods and compositions for using IL-32 as a target for screening drugs that can alter proinflammatory cytokine responses (e.g., TNFα production).

A technique for drug screening provides high throughput screening for compounds having suitable binding affinity to IL-32 peptides and is described in detail in WO 84/03564, incorporated herein by reference. Briefly, large numbers of different small peptide test compounds are synthesized on a solid substrate, such as plastic pins or some other surface. The peptide test compounds are then reacted with IL-32 peptides and washed. Bound IL-32 peptides are then detected by methods well known in the art.

Another technique uses IL-32 antibodies, generated as discussed above. Such antibodies capable of specifically binding to IL-32 peptides compete with a test compound for binding to IL32. In this manner, the antibodies can be used to detect the presence of any peptide that shares one or more antigenic determinants of the IL-32 peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with IL-32 and variants or mutants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level.

In second messenger assays, the host cells are preferably transfected as described above with vectors encoding IL-32 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); U (units), mU (milliunits); min. (minutes); sec. (seconds); % (percent); kb (kilobase); bp (base pair); PCR (polymerase chain reaction).

In addition, the following cells and bioassays were employed. The human NK cell line was obtained from Dr. Hans Klingerman (Rush Medical Center, Chicago, Ill.) and cultured in RPMI1640 medium containing 10% FCS, IL-2 (50 pg/ml) and IL-15 (200 pg/ml) (Peprotech, Rocky Hill, N.J.). Mouse macrophage Raw 264.7 cells, human A549 lung carcinoma, monkey Cos7 kidney cells, Anjou65 (subclone of the human fibroblast 293T line), human epithelial Wish cells, and the human monocyte THP-1 cell line were obtained from American Type Culture Collection (ATCC) and maintained according to supplied instructions. Bioassays were performed in 96 well plates.

Briefly, Raw cells ($5 \times 10^5$/ml, 0.1 ml/per well), A549-Rβ cells ($2 \times 10^5$/ml, 0.1 ml/per well), and human NK cells ($5 \times 10^5$/ml, 0.1 ml/per well) were seeded in 96 well plates and cultured until cells adhered to the plates. For Raw cell assays, spent medium was removed and the cells were stimulated with fresh medium (0.2 ml) containing various concentration of rIL-32 in the presence 5 µg/ml polymyxin B (Bedford Laboratories, Bedford, Ohio). For the A549-Rβ cell assays, spent medium was removed and cells were stimulated with fresh medium (0.2 ml) containing IL-18 (produced as described by Kim et al., *J Immunol*, 166:148-154, 2001). For the NK cell assays, cells were stimulated with IL-12 (Peprotech) or IL-18, or both cytokines. THP-1 cells ($5 \times 10^5$/ml, 0.1 ml/per well) were seeded in 96 well plates in the absence of FCS, and then stimulated with rIL-32 from various sources. For phorbol 12-myristate 13-acetate (PMA) THP-1 differentiation assays, THP-1 cells ($0.25 \times 10^5$/ml, 0.1 ml/per well) were seeded in 24 well plates and then stimulated with 100 ng/ml PMA (Sigma, St Louis, Mo.) for 48 hr, before washing cells in medium lacking FCS, and treating the cells with rIL-32. The plates were placed in a cell culture incubator for 16-20 hours and then the culture supernatants were collected for cytokine measurement.

Human peripheral blood mononuclear cells (PBMC) were isolated from residual leukocytes following platelet-pheresis of healthy donors using Histopaque (Sigma) that was approved by the Combined Colorado Investigational Review Board. PBMC ($1.5 \times 10^7$) were seeded in 6 well plates in 3 ml of RPMI containing 10% FCS, and then stimulated with 20 µg of Con A (Sigma). The plates were placed in a cell culture incubator for 60 hours, after which time the culture supernatant and cell lysate were collected for IL-32 measurement.

IL-32 was evaluated in terms of units of biological activity, because there were differences in activity levels between rIL-32 produced in *E. coli*, and rIL-32 produced in mammalian cells, and because there were differences in activity levels between the different batches. One unit of IL-32 is defined as the amount of IL-32 that induces a 2-fold induction of human or mouse TNFα in PMA-differentiated THP-1 cells and mouse Raw cells, respectively, under the assay conditions described above. The approximate concentration of 1 unit of *E. coli* rIL-32 amounted to 20 ng/ml, while the approximate concentration of 1 unit of mammalian rIL-32 amounted to 0.1 ng/ml (as calculated by ECL and Western blot).

EXAMPLE 1

Identification of IL-18 Inducible Genes, including NK4/IL32

Wild type human A549 lung carcinoma cells (A549-WT) express IL-18Rα but not IL-18Rβ. Thus, in order to express a functional IL-18 receptor in A549 cells, A549 cells were transfected with an IL-18Rβ chain expression vector. Briefly, human lung carcinoma A549 cells ($3 \times 10^5$ per well) were seeded in 6 well plates a day before transfection. The cells were then washed with 2 ml of Opti-MEM (Invitrogen, Carlsbad, Calif.) and incubated for 25 min in 1 ml of fresh medium. The transfection mixture solution for each well was prepared by mixing 5µl of Lipofectamine 2000 in 100 µl of Opti-MEM followed by a 5 min incubation in the tissue culture hood. Next, 2 µg of plasmid DNA, pTARGET/huIL-18β (Kim et al., *J Immunol*, 166:148-154, 2001), was added, followed by a 20 min incubation period. The transfection mixture solution was added to the wells and the plate was incubated for an additional 4 hours at 37° C. Transfection was terminated, by the addition of 2 ml of cell culture medium containing 10% FCS to each well. The next day, cells were trypsinized and transferred to a 15 cm plate. After cells adhered to the plate, the culture medium was replaced with fresh medium containing 800 µg/ml of Neomycin (G418, Invitrogen). The selection medium was exchanged every three days with fresh medium until individual colonies appeared (~10-14 days). Small pieces of circular 3 MM papers were sterilized, wetted with trypsin, and then used for picking individual colonies. Colonies were transferred into 24 wells plate containing 1 ml of selection medium in each well. Individual clones were grown until $10^6$ cells were obtained, and then each clone was tested for expression of the transfected gene by RT-PCR, as well as in bioassays measuring IL-6 and IL-8 in cell culture medium after IL-18 stimulation for 24 hours. Three clones were positive by both RT-PCR and bioassay. Limiting dilutions cultures were prepared in order to obtain a single clone.

As shown in FIG. 1 panel A, A549 cells transfected with an IL-18Rβ (A549-Rβ) construct (Kim et al., *J Immunol*, 166: 148-154, 2001) expressed both the IL-18Rα and IL-18Rβ chains as determined by RT-PCR. The stable clone (A549-Rβ) was tested for induction of IL-8 after IL-18 (100 ng/ml) stimulation for 16 hours. Upon the expression of IL-18Rβ in A549 cells, the A549-Rβ cells responded to IL-18 in the absence of a co-stimulus by producing IL-6 and IL-8, whereas the A549 parent cell line (A549-WT) remained unresponsive to IL-18 (See, FIG. 1, panels B and C, N=7).

The A549-Rβ cells were then used to study IL-18 inducible gene expression by microarray. Briefly, A549-Rβ cells were seeded at $2 \times 10^6$ in nine cm plates one day before the experiment. The cells were then stimulated with IL-18 (50 ng/ml) for 6 hours, at which time the treated cells and controls were harvested. Total RNA was isolated with Tri-Reagent, and purified with the RNeasy kit (Qiagen, Valencia, Calif.). The total RNA was then used for microarray analysis per instructions from Affymetrix. Total RNA (10 µg/ml) was converted to first strand cDNA using Superscript II RT (Invitrogen). The second strand cDNA was synthesized with the use of T4 DNA polymerase I. After second strand synthesis, the reaction mixture was cleaned with a kit supplied by GeneChip. cRNA synthesis was performed to generate biotin-labeled cRNA using a RNA transcript-labeling kit. The biotinylated-cRNA was fragmented prior to hybridization. The samples were hybridized to the Affymetrix GeneChip HG-U133, and data was analyzed in the microarray core laboratory of the University of Colorado Health Sciences Center.

The microarray data revealed that IL-18 induced several cytokine genes including IL-6 and IL-8. Several chemokines including interferon-β2 and IL-1β, whose expression was previously known to be IL-18 inducible, were among the group observed to have an increase in expression of greater than 3-fold (log base 2) in response to IL-18 treatment (See, Table 1 showing data from two independent experiments). Interestingly, natural killer cell transcript 4 (NK4) was also highly induced (5.3-fold). The NK4 gene was originally described as an activated NK or T cell product (Dahl et al., *J Immunol*, 148:597-603, 1992), although no functional data had been collected on this gene. Expression of NK4 mRNA was also examined by RT-PCR, using the same total RNA as was used for the microarray study. The first strand cDNA was synthesized from approximately 1 μg total RNA, using SuperScript II from Invitrogen (Carlsbad, Calif.). The PCR reaction was performed at 94° C. for 45 s, 70° C. for 2 min, 59° C. for 1 min for 30 cycles with a sense primer, 5'-CTGTCCCGAG TCTGGACTTT-3' (SEQ ID NO:1) and an antisense primer, 5'-GCAAAGGTGG TGGTCAGTAT C-3' (SEQ ID NO:2). The NK4 transcript was detected in IL-18 treated A549-Rβ cells, but not unstimulated A549-R, cells (See, FIG. 1, panel D).

TABLE 1

IL-18 Inducible Genes Identified By Microarray Analysis

| GenBank Accession No. | Fold Increase | Gene Name |
|---|---|---|
| M28130 | 8.6 | Interleukin-8 (IL-8) |
| U64197 | 8.0 | Chemokine exodus-1 |
| X04430 | 7.7 | Interferon-β2 (IL-6) |
| U81234 | 5.8 | Chemokine-α3 (CKA-3) |
| U37518 | 5.3 | TNF-related apoptosis inducing ligand (TRAIL) |
| AB007872 | 5.3 | TNFα inducing factor (TAIF, NK4) |
| X54489 | 5.0 | Melanoma growth stimulatory activity (MGSA) |
| M36821 | 4.6 | GRO-γ |
| X03656 | 4.0 | Granulocyte colony stimulating factor (G-CSF) |
| Z70276 | 3.7 | Fibroblast growth factor 12 |
| M36820 | 3.2 | GRO-β |
| X04500 | 3.5 | Prointerleukin-1β |
| J04513 | 3.1 | Basic fibroblast growth factor (bFGF) |

NK4 gene expression was also examined in the NK92 cell line (Hoshino et al., *J Immunol*, 162:51-59, 1999). The NK4 gene was constitutively and highly expressed in this cell line, when maintained in a condition medium containing both IL-2 and IL-15. The IL-2 in the condition medium is contemplated to contribute to the high level of NK4 gene expression observed in the NK92 cells line.

EXAMPLE 2

TNFα Induction by Recombinant NK4/IL-32

To determine the function of this poorly described gene product, the NK4 cDNA (See, FIG. 3, IL-32α) was cloned from NK92 cells (Dahl et al., supra, 1992, herein incorporated by reference in its entirety) into pGEMT-Easy (Promega) for sequencing, and then the insert was transferred to pPROEX/Hta (Invitrogen) for expression in *E. coli* or to pTARGET (Promega) for mammalian expression. Recombinant NK4 was expressed in *E. coli* and purified with a TALON affinity column (Invitrogen) by introducing a His[6] tag at the N-terminus of the recombinant proteins. The TALON affinity-purified protein was subjected to size exclusion chromatography (Superdex 75, ÄKTAFPLC), and digested with Tobacco Etch Virus (Invitrogen) for 16 hrs at 4° C. to remove the His[6] tag. The cleaved recombinant proteins were dialyzed in phosphate buffer (20 mM, pH 9). This material was later subjected to ion exchange chromatography (HiTrapQFF, ÄKTAFPLC). The recombinant NK4 protein purified using three sequential steps (His-tag affinity chromatography, size exclusion chromatography and ion exchange chromatography) ran as a homogenous band of approximately 20 kDa in a 10% SDS-PAGE gel, subsequently stained with Coomassie blue (See, FIG. 2, panel A).

The thrice-purified recombinant NK4 protein was then tested for biological activity by measuring TNFα secretion by mouse Raw 264.7 macrophage cells in the presence of polymyxin B (100 U/ml). Mouse Raw 264.7 macrophage cells responded to recombinant NK4 and by producing a large amount of TNFα, coinciding with the peak fractions of protein eluting from the ion exchange column (See, FIG. 2, panel A). In recognition of the newly discovered biological activity of NK4, the molecule was renamed IL-32/TNFα-inducing factor (TAIF). As shown in FIG. 2 panel B, IL-32α induced significant amounts of TNFα, at IL-32α concentrations as low as 400 pg/ml (27 picomoles based on the 14.8 kDa calculated molecular weight of IL-32α), and increased TNFα production in a dose dependent manner. TNFα is well known to possess multiple inflammatory properties that play a causative role in numerous inflammatory and autoimmune diseases (Beutler et al., *Blood Cells Mol Dis*, 24:216-230, 1998).

Recombinant IL-32α was also produced in mammalian cells, by transient-transfection of Cos-7 cells (8×10[6]) with the pTARGET/IL-32β expression vector via the DEAE-dextran technique (Sompayrac et al., *Proc Natl Acad Sci USA*, 78:7575-7578, 1981). As shown in FIG. 2 panel C, recombinant IL-32α (100 pg/ml) obtained from the concentrated supernatant of IL-32α-transfected cells induced TNFα production, whereas the concentrated supernatant from mock-transfected cells did not. The concentration of recombinant IL-32α in Cos-7 supernatants was estimated via ECL and immunoblot. Additionally, IL-32α produced in mammalian cells was found to possess greater TNFα-inducing activity than did recombinant IL-32α produced in bacterial cells.

EXAMPLE 3

Identification of IL-32 Genomic Structure and Splice Variants

Figure 5:
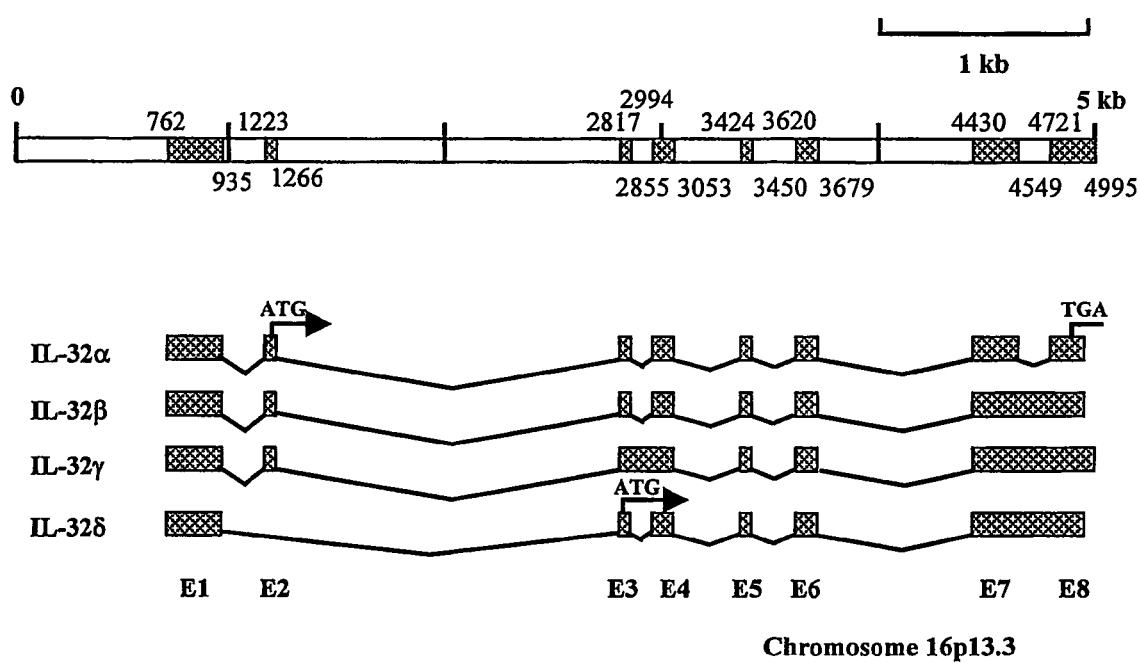
FIG. 5 depicts the structure of the human IL-32 gene on chromosome 16p13.3, with exons depicted by stippled boxes. The numbers above and below the schematic of the IL-32 gene delineate the eight exons, while the sequence of this 5 kb genomic fragment is disclosed herein as SEQ ID NO:11. Splicing of the four IL-32 variants (α, β, γ and δ) is also shown.

The structure of the IL-32 gene and its localization within the human genome was analyzed. IL-32 was also cloned by RT-PCR from the human NK92 cell line, cultured in the presence of IL-2 (50 pg/ml), and IL-15 (200 pg/ml). The following primers were used for this purpose: sense 5'-CTGTCCCGAG TCTGGACTTT-3' (SEQ ID NO:1), and antisense 5'-GCAAAGGTGG TGGTCAGTAT C-3' (SEQ ID NO:2). As shown in FIGS. 3 and 5, three splice variants of IL-32 (IL-32α disclosed as SEQ ID NO:3 and GENBANK Accession No. AY495331, IL-32β disclosed as SEQ ID NO:4 and GENBANK Accession No. AY495332, and IL-326 disclosed as SEQ ID NO:5 and GENBANK Accession No. AY495333) were identified from RNA derived from NK92 cells, whereas a different splice variant (IL-32γ disclosed as SEQ ID NO:6 and GENBANK Accession No. BK004065)

had been previously reported as the NK4 transcript (GENBANK Accession No: NM_004221). Thus, IL-32 is expressed as at least four variants due to alternative mRNA splicing.

The blast program from the NCBI web site was used to determine that the IL-32 gene resides on chromosome 16p13.3. Approximately 5 kb of sequence encompassing the IL-32 gene (set forth as SEQ ID NO:11 and GENBANK Accession No. AY495334) was identified from a 180 kb stretch of human chromosome 16 sequence (GENBANK Accession No. AC108134). By comparing the sequences of the splice variants with the genomic sequence, the IL-32 gene was found to contain eight small exons, with the second and third exons possessing ATG start codons. IL-32γ has an additional 46 amino acids at its N-terminus (SEQ ID NO:14) because of the absence splicing between exons 3 and 4. However in IL-32δ, the second exon is absent, resulting in the use of the ATG start codon in the third exon, instead of the ATG in the second exon. IL 32α was the most abundant cDNA clone, therefore this isoform was used for many of the experiments described herein. IL-32α has a deletion of 57 amino acid residues at its C-terminus due to splicing between exons 7 and 8, which is in contrast to the other variants that have a single large exon encoding their C-termini. The analysis of the IL-32 amino acid sequences revealed the presence of three potential N-myristoylation sites and one potential N-glycosylation site (See, FIG. 4A).

The Blast program was used to search the NCBI database for homologs of IL-32. In this way, expressed sequence tag (EST) clones of equine, bovine, ovine, and swine IL-32 were identified. The equine IL-32β protein sequence (GENBANK Accession Nos. CD469554 and BI961524) shares the highest homology with the human sequence (31.8% identity), followed by bovine (GENBANK Accession Nos. CK834399 and CK832489), ovine (GENBANK Accession No. CO202364), and swine (GENBANK Accession No. CB287292) sequences. The alignments of human, equine, and bovine IL-32β protein sequences are shown in FIG. 4B). In particular, isoform A of sheep and pigs has been identified, while both isoforms A and B have been identified in horses, and isoforms B and C have been identified in cows. The sequences of equine IL-32β and bovine IL-32γ were each combined from two EST clones, and the open reading frames were deduced from the combined sequence.

EXAMPLE 4

Analysis of 1-32 Expression

Figure 8:
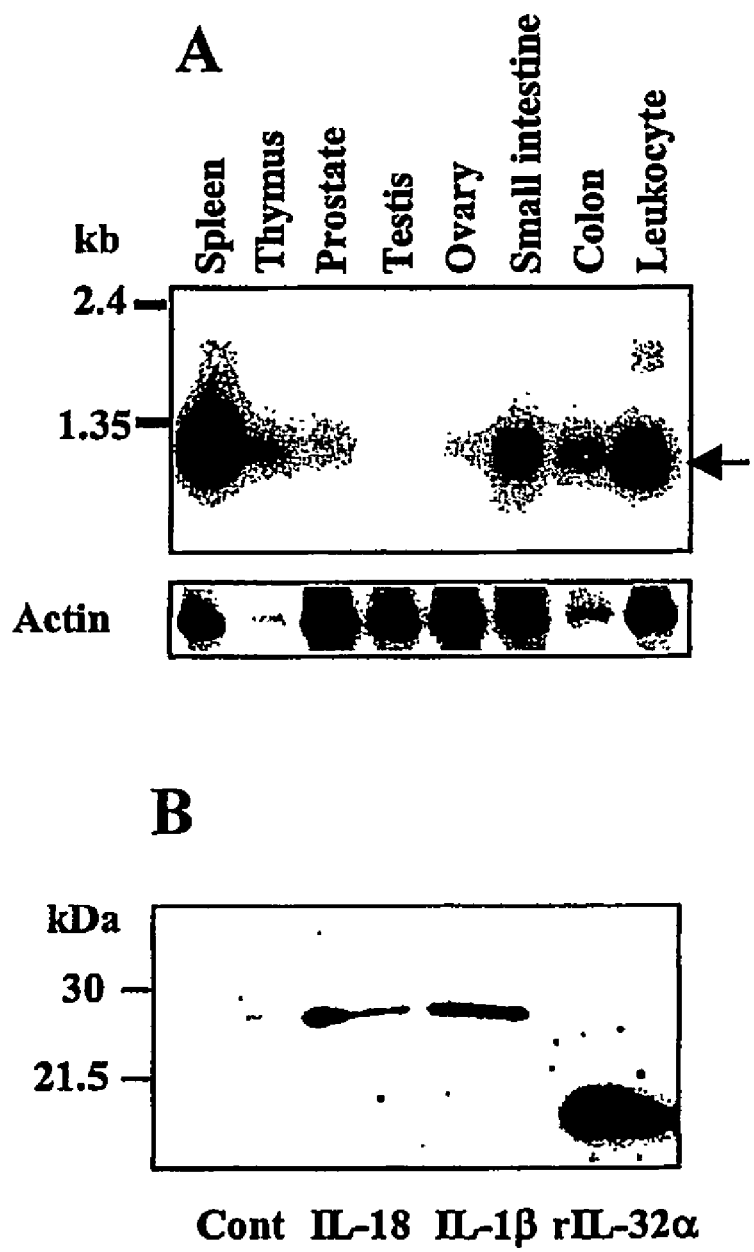
FIG. 8 depicts the endogenous expression of IL-32 at both mRNA and protein levels. Panel A shows the expression of IL-32 mRNA in various human tissues as determined by Northern blot. The numbers on the left indicate mRNA size. Panel B shows that soluble IL-32 is present in cell culture supernatants as determined by Western blot. A stable A549-Rβ clone was stimulated for 48 h in the presence of IL-18 (50 ng/ml) or IL-1β (10 ng/ml), in the absence of FCS as indicated. The supernatants were harvested and probed with an affinity-purified anti-IL-32α antibody.

The expression of IL-32 in various human tissues was examined by northern blot. Briefly, IL-32α and actin cDNA inserts were excised from plasmid vectors by using suitable restriction enzymes, size-fractionated and purified with a GeneClean II kit (Q-BIO gene, Carlsbad, Calif.). The cDNAs were labeled with $^{32}$P-dCTP (NEN Life Science, Boston, Mass.) by random priming using the Klenow enzyme (New England Biolabs, Beverly, Mass.). A membrane containing human poly(A)$^+$ RNA from different tissues (human MTN Blot II) incubated with the cDNA probes, whose binding was detected by autoradiography. As shown in FIG. 8A, a 1.2 kb IL-32 transcript was detected in most tissues, with higher levels of IL-32 detected in immune cells as compared to other cell types. The high expression of IL-32 mRNA in immune tissues was not due to loading differences as shown by reprobing the blot with an actin fragment.

Endogenous IL-32 expression was also detected at the protein level. Briefly, A549-Rβ cells were seeded at $10^6$ cells/well in 6 well plates. After the cells had adhered to the plate, the F12K culture medium was removed and replaced with serum-free medium, which in some wells contained IL-18 (50 ng/ml), IL-1β (100 ng/ml) or LPS (500 ng/ml). After 48 hrs, the supernatants were harvested and concentrated 10 times with Centricon concentrators. As shown in FIG. 8B, an approximately 30 kDa species corresponding to endogenous IL-32 was detected by immunoblot with an affinity-purified rabbit anti-human IL-32α polyclonal antibody. The difference in molecular weight between rIL-32 from E. coli, and endogenous IL-32 is contemplated to be due to post-translational modification of the endogenous molecule, since analysis of the amino acid sequence revealed the presence of potential N-linked glycosylation and myristoylation sites. IL-32 was secreted into the cell culture medium of cells treated with IL 18 (100 ng/ml), IL-1β (100 ng/ml) or LPS (500 ng/ml), but not by unstimulated cells (control). IL-32 was detected in cell culture medium as a secreted molecule, although IL-32 does not possess a typical hydrophobic signal peptide at its N-terminus. IL-18 induced IL-32 expression to a greater extent than did IL-1β or LPS. A 60 kDa band was also observed (not shown), which is contemplated to be a dimerized form of IL-32. Like the monomer, the 60 kDa band was found in the supernatants of treated cells, but was absent from that of unstimulated cells.

Induction of IL-32 in human epithelial Wish cells treated with IFNγ since was also examined, since Wish cells are commonly used for antiviral assays and for assessments of other biological activities of IFNγ. For time courses of IL-32 production, Wish, A549-WT, and A549-Rβ cells were seeded at $5 \times 10^4$ cells/well in 6 well plates, incubated overnight and then stimulated with IFNγ (100 U/ml), IL-18 (50 ng/ml) or IL-1β (10 ng/ml). Affinity purified rabbit anti-IL-32α was used for detecting IL-32 in cell culture medium by inimunoblot. Peroxidase-conjugated secondary antibodies (Jackson ImmunoResearch Laboratories, West Grove, Pa.) were used to develop the blots using enhanced chemiluminescence (NEN Life Science). For IL-32 detection by electrochemiluminescence (ECL), an aliquot of the affinity purified anti-IL-32α antibody was labeled with biotin, and another aliquot was labeled with ruthenium according to the manufacturer's instructions (Igen, Gaithersburg, Md.). The biotin and ruthenium labeled antibodies were used to construct a standard curve using recombinant IL-32α. The liquid-phase ECL method was used to measure various cytokines in cell culture media and in serum samples. The amount of electrochemiluminescence was determined using an Origen Analyzer (Igen).

Figure 9:
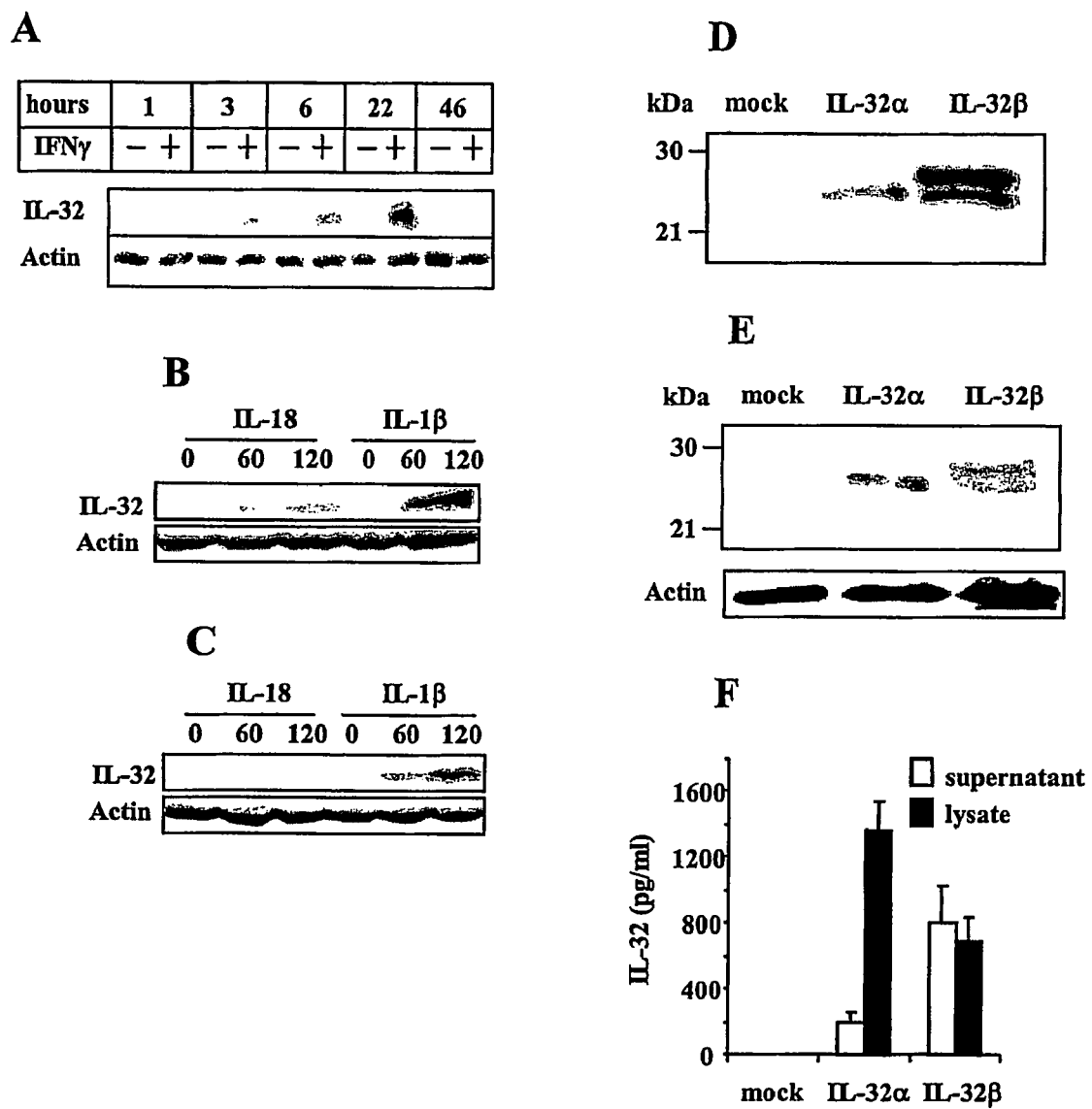
FIG. 9 shows the detection of IL-32 in cell lysates. IL-32 production by Wish cells (panel A), A549-Rβ cells (panel B) and A549-WT cells (panel C) upon stimulation with IFNγ (100 U/ml), IL-18 (50 ng/ml) or IL-1β (10 ng/ml) are shown. The data represent one of four independent experiments. IL-32 expression upon transient transfection of Cos7 cells with IL-32α and IL-32β cDNAs was detected in cell culture supernatants (panel D) and cell lysates (panel E) by immunoblot. Panel F provides a comparison of IL-32 concentration in supernatants and lysates as measured by ECL. The data represent the mean±SEM of five separate experiments.

As shown in FIG. 9A, IL-32 was induced in cell lysates of human epithelial cells in a time dependent manner, diminishing after 46 hours, whereas IL-32 was not induced in unstimulated cells. Similarly, IL-18 and IL-1β increased the expression of endogenous IL-32 in the lysates of A549-Rβ cells in a time dependent manner (FIG. 9B) whereas IL-32 was only induced by IL-1β in A549-WT cells (FIG. 9C). In addition, IFNγ was also observed to induce IL-32 in the lysates of A549-WT cells (data not shown).

In order to determine whether the recombinant proteins expressed from the cDNAs of IL-32α and β in mammalian cells were comparable to endogenous IL-32, Cos7 cells were transiently transfected with IL-32α and β cDNAs. As shown in FIGS. 9D and 9E, recombinant IL-32α and IL-32β were present in both cell culture media and lysates of the transfected cells as determined by immunoblot. The molecular size of recombinant mammalian IL-32 in the immunoblots was identical to the molecular size of the endogenous IL-32 shown in FIG. 8B. The ECL assay revealed a similar distribution of IL-32α and IL-32β in the culture media and lysates, although IL-32β appears to be more efficiently secreted as compared to IL-32α, which was predominantly cell-associated.

The polyclonal anti-human IL-32 antibody was affinity purified over a column containing IL-32α-immobilized on agarose beads (Affi-gel 15). Peroxidase conjugated anti-rabbit immunoglobulin secondary antibodies were obtained from Jackson ImmunoResearch. Since the anti-human IL-32 antibody specifically recognizes endogenous IL-32, the IL-32 level in the sera of human subjects (healthy individuals and patients with sepsis) was measured by ECL. Although IL-32 was detected in sera of healthy individuals (5 of 42 samples), the IL-32 levels were less than 70 pg/ml. In contrast, the mean IL-32 levels in sera of patients with sepsis were 35-fold higher than that of sera from healthy individuals. For the first time during development of the present invention, IL-32 is shown to be an inflammatory cytokine produced (directly or indirectly) in response to bacterial infection. In addition, IL-32 was detected in patients with active rheumatoid arthritis indicating that it also plays a role in autoimmunity.

Figure 10:
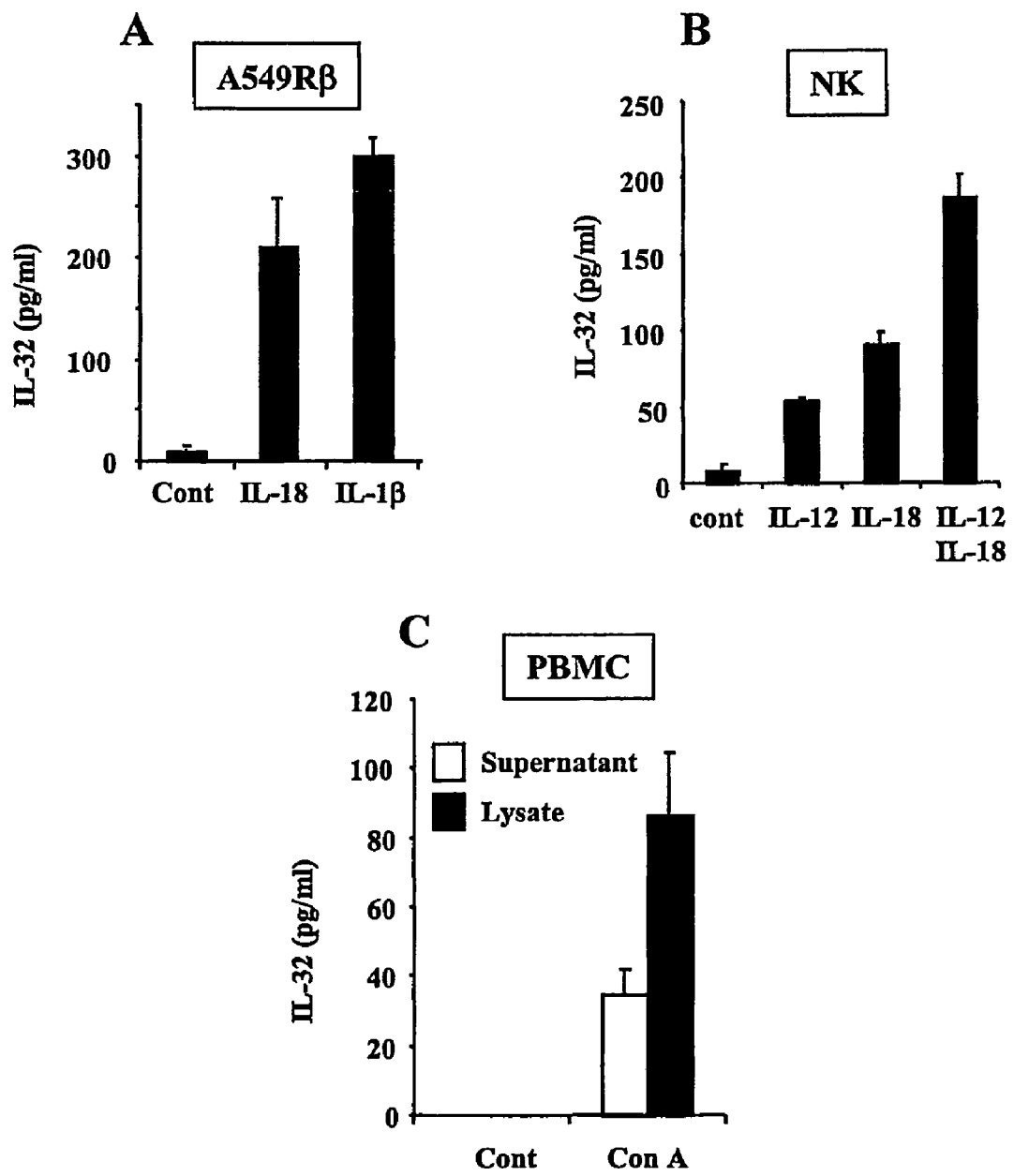
FIG. 10 depicts the measurement of endogenous IL-32 by electrochemiluminescence (ECL). In panel A, IL-32 was detected by ECL assay in the same samples used for immunoblot in FIG. 9B. In panel B, IL-32 was detected in the supernatant of a human NK cell line after treatment with IL-12, IL-18, or IL-12 plus IL-18. The data represent mean±SEM of 4 separate experiments. In panel C, ConA induced-IL-32 was detected in both the supernatant and lysate of human PBMC (N=7).

To examine the regulation of IL-32 production, IL-32 was measured in the cell culture medium of different cell lines, as well as human PBMC. IL-32 was detected in the cell culture medium of A549-Rβ cells after IL-18 or IL-1β stimulation but not in control medium (FIG. 10A). Since the NK4 (IL-32) gene was isolated from IL-2-activated NK cells, the human NK cell line was stimulated with a combination of IL-12 plus IL-18. As shown in FIG. 10B, there was a significant induction of IL-32 by IL-12 or IL18 in NK cells, and the effect of the combination of these two cytokines appeared to be additive. By comparison, when this cell line was stimulated by either IL-12 or IL-18, there is little or no induction of IFNγ, whereas IFNγ production by the combination of IL-12 plus IL-18 is highly synergistic (Kim et al., *J Biol Chem*, 277: 10998-11003, 2002). The induction of IL-32 (via IFNγ) was examined by stimulating NK cells with IL-12 and IL-18, in the presence of a neutralizing anti-IFNγ antibody. This combination had no effect on IL-32 induction (data not shown). Human peripheral blood mononuclear cells (PBMC) contain mostly T-cells with few numbers of monocytes and B-cells. Freshly prepared PBMC were stimulated with LPS or ConA and the supernatants and lysates were harvested and assayed for IL-32 concentration. After 60 hours, there was no detectable IL-32 in the supernatants or lysates of PBMC stimulated with LPS (data not shown). However, ConA consistently induced IL-32, which was found in the supernatants and lysates. As shown in FIG. 10C, the lysates contained more IL-32 than the supernatants.

EXAMPLE 5

Identification of IL-32 Responsive Signal Transduction Pathways

This example provides details of the experiments conducted to assess the effect of the cytokine IL-32 on signal transduction molecules inhibitor of kappa B (IκB) and p38 mitogen-activated protein kinase (MAPK). Briefly, mouse RAW 264.7 macrophage cells were stimulated with IL-32α (50 ng/ml) in the presence of 5 μg/ml polymyxin B (Bedford Lab, Bedford, Ohio) for the indicated amount of time (in minutes). Cells were lysed with kinase lysis buffer (Han et al., *J Biol Chem*, 277:47167-47174, 2002). The cell contents were separated in a 10% SDS-PAGE gel and transferred to a nitrocellulose membrane, which was subsequently blocked with 3% BSA. The membrane was probed with rabbit anti-IκB and normalized with goat anti-actin (Santa Cruz Biotechnology, Santa Cruz, Calif.). As shown in FIG. 11A, IL-32α induced IκB degradation in a time dependent manner, beginning 15 min after treatment and reaching a maximal level at 45 min, followed by recovery after 90 min.

The membrane was also probed with rabbit anti-phospho-p38 MAPK and normalized with rabbit anti-p38 MAPK (Cell Signaling, Beverly, Mass.). As shown in FIG. 10B, phosph-p38 MAPK was dramatically increased 5 min after stimulation by IL-32α and then decreased from 15 min to 30 minutes, thereafter. Interestingly, a second increase in p38 MAPK phosphorylation was observed at 45 min, which decreased more slowly.

EXAMPLE 6

Identification of IL-32 Binding Proteins

Recombinant IL-32α (or IL-32β, IL-32δ and IL-32γ) is expressed in *E. coli* and purified using three sequential steps as described in Example 2. Approximately 5 mg of the purified IL-32α is immobilized onto Affi-gel 15 agarose beads (Bio-Rad Laboratories, Hercules, Calif.). Various potential receptor sources are applied to the IL-32α-affinity column (e.g., human serum or lysates of cells which secrete TNFα in response to IL-32α, such as Raw 264.7 cells). The IL-32α affinity column is washed extensively and the IL-32 receptor is then eluted with an elution buffer (e.g., 50 mM citric acid, 100 mM NaCl, pH 2.5). The eluted fractions are neutralized immediately with 2 M tris base. The IL-32 binding proteins isolated in this way are further characterized by chemical analysis (e.g., peptide sequence analysis through Edman degradation and/or mass spectroscopy) and bioassay (e.g., purified or recombinant receptors are tested for their ability to block IL-32α-induced TNFα secretion by Raw 264.7 cells). It is contemplated that authentic IL-32 binding proteins have the ability to inhibit IL-32 biological activities (similar to what has been observed with the TNFBP). It is also contemplated that other types of authentic IL-32 binding proteins have the ability to enhance IL-32 biological activities (similar to what has been observed with the IL-6 ligand binding chain).

EXAMPLE 7

Therapeutic Effect of IL-32-Antibodies and IL-32 Inhibitors in a Murine Model of Arthritis This example provides details of the experiments conducted to assess the effect of IL-32-antibodies and IL-32 antagonists (e.g., soluble IL-32 receptors, dominant-negative IL-32 variants, small molecule inhibitors, etc.) as therapeutics for the treatment of collagen-induced arthritis (CIA) in mice. Briefly, CIA is induced in 8 to 10 week old DBA/1J mice (Jackson Laboratories, Bar Harbor, Me.) by intradermal injection of type II bovine collagen (CII) as known in the art (Banda et al., *Arthritis Rheum*, 46:3065, 2002). Each mouse receives 100 μl injections containing 200 μg CII and 200 μg of inactivated *Mycobacterium tuberculosis* (Difco, Detroit, Mich.) in incomplete freund's adjuvant on days 0 and 21. Mice are treated between days 21 and 42 with one of three therapies given as IP injections every 3 days: 2 mg/mouse normal rabbit IgG; 2 mg/mouse neutralizing rabbit anti-IL-32 prepared using HiTrap Protein G HP (Amersham Pharmacia Biotech AB, Uppsala, Sweden); and 2 mg/mouse recombinant IL-32 antagonist (e.g., IL-32 receptor-IgG1 Fc fusion protein or dominant-negative IL-32 variant). The mice (5 in each group and 5 untreated mice) are sacrificed on day 42 by anesthesia and cervical dislocation.

The clinical disease activity of CIA is assessed every other day between days 21 and 42 by blinded observers using a three-point scale for each paw; 0=normal joint; 1=slight inflammation and redness; 2=severe erythema and swelling affecting the entire paw with inhibition of use; and 3=deformed paw or joint, with ankylosis, joint rigidity, and loss of function. The total score for clinical disease activity is based on all four paws, with a maximum score of 12 for each animal. After sacrifice, both forepaws and the right hand limb are surgically removed on day 42 and fixed in 10% buffered formalin with preparation of tissues samples and histological analysis as known in the art (Bendele et al., *Arthritis Rheum*, 43:2648, 2000). An experienced observer (blinded to the treatment) scores the histological findings in paws, ankles, and knees. The data are expressed as mean scores for inflammation, pannus, cartilage damage, and bone damage, as well as an overall score, based on scales of 0 to 5.

Using published methods (Banda et al., *J Immunol*, 170: 2100-2105, 2003), various immune parameters are measured, including but not limited to: CII-specific proliferation by spleen and lymph node cells, production of anticollagen antibodies, CII-induced cytokine secretion by spleen cells (e.g., utilizing TNFα, IFNγ, IL-1β, IL-1Ra and IL-10 ELISAs), and steady state cytokine mRNA levels in joints (e.g., TNFα, IFNγ, IL-1β, IL-1Ra, IL-6, Il-18, MIF, TNFβ, LTβ, TGFβ1, TGFβ2). Some preferred embodiments of the present invention comprise a IL-32 antibody or a IL-32 antagonist that reduces clinical disease activity scores and histological scores of joint damage, by at least 50% (more preferably by at least 75%, and most preferably by at least 90%). Other preferred embodiments comprise an IL-32 antibody or an IL-32 antagonist that reduces CII-induced lymphocyte proliferation, and/or serum levels of collagen binding IgG antibodies, by at least 50% (more preferably by at least 75%, and most preferably by at least 90%). Particularly preferred embodiments, comprise an IL-32 antibody or an IL-32 antagonist that reduces steady state mRNA levels of TNFα, IFNγ, and/or IL-1β in isolated joints, by at least 50% (more preferably by at least 75%, and most preferably by at least 90%). Importantly, preferred embodiments comprising the IL-32 antibodies or IL-32 antagonists described herein, are contemplated to find use in the treatment of human rheumatoid arthritis patients, using methods similar to that employed for administration of TNF-reactive antibodies (infliximab/REMICADE and adalimumab/HUMIRA) and soluble TNF-receptor/immunoglobulin fusion proteins (etanercept/ENBREL).

EXAMPLE 8

Biological Activity of Recombinant IL-32

Figure 6:
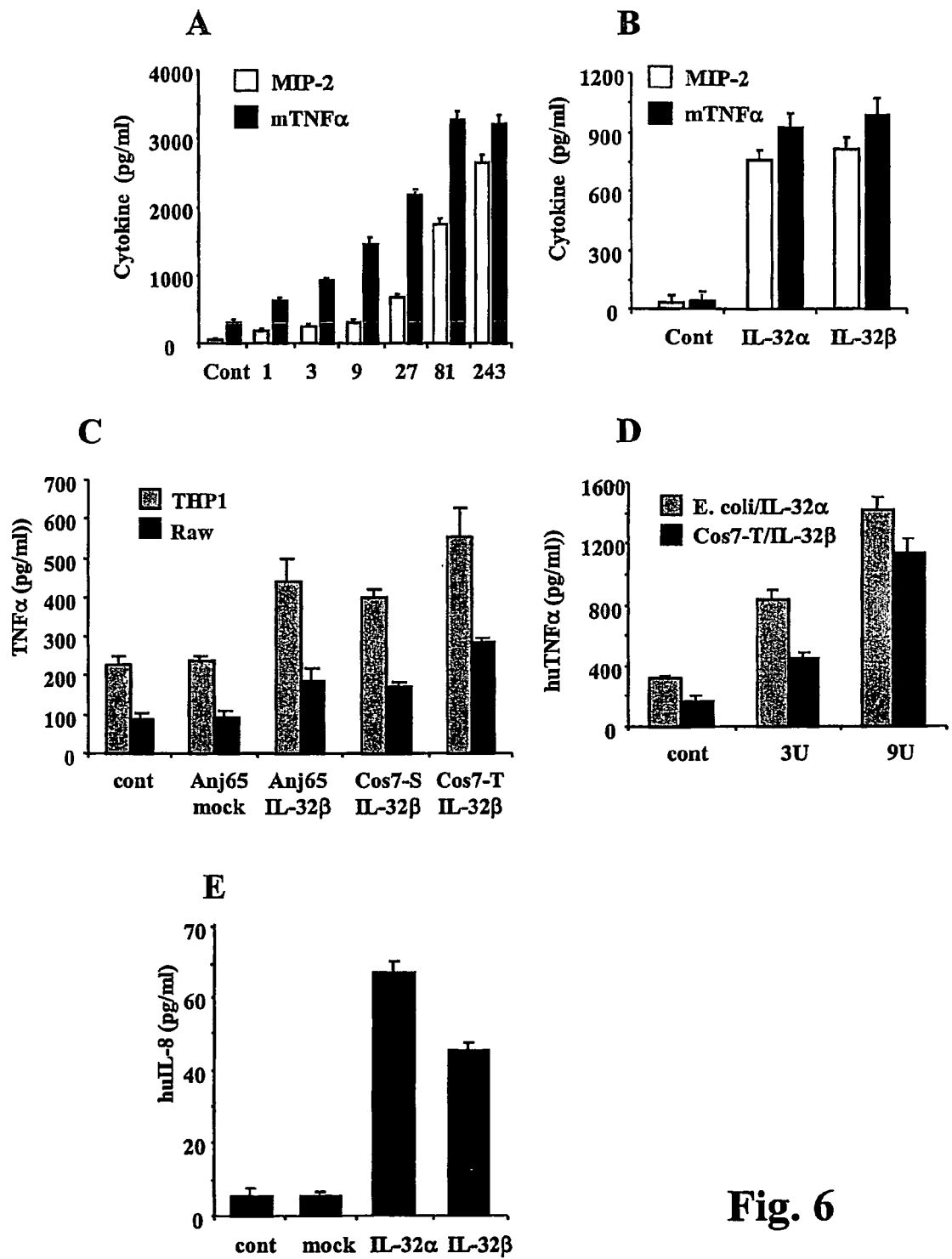
FIG. 6 illustrates that rIL-32 induces proinflammatory cytokines in both macrophage cells (Raw) and monocytes (THP-1). Panel A indicates that rIL-32α produced in E. coli induces both MIP-2 and TNFα secretion in a dose-dependent manner. IL-32 concentrations are indicated in units/ml on the x-axis. Panel B shows that both IL-32α (10 U/ml) and IL-32β (10 U/ml) variants activate mouse Raw 264.7 macrophage cells. Panel C provides a graph of human and murine TNFα induced by various sources of IL-32β. Raw cells and PMA-differentiated-THP-1 cells were treated with 1 U/ml of Anjou65 and Cos-7S, or 2 U/ml of Cos7-T. IL-32α produced in E. coli and IL-32β produced in mammalian cells induced TNFα expression in PMA-differentiated THP-1 cells in a dose-dependent manner. Panel E illustrates that high concentrations of *E. coli* rIL-32α (20 U/ml) or mammalian rIL-32β (Anjou65, 10 U/ml) induce IL-8 secretion in undifferentiated THP-1 cells.

IL-32α induced significant amounts of TNFα and MIP-2 and increased the production of both cytokines in a dose dependent manner as shown in FIG. 6A. The biological activity of IL-32α as then compared with that of IL-32β which has a full C-terminus. IL-32β induced similar the levels of TNFα and MIP-2 as did IL-32α in the mouse macrophage Raw cell line (FIG. 6B). Although all the experiments were performed in the presence of polymyxin B (5 μg/ml), the possibility of endotoxin contamination of the recombinant proteins produced in *E. coli* could not be ruled out.

Recombinant IL-32 was also produced in a mammalian system in order to avoid endotoxin contamination. The rIL-32β was produced from three different sources of mammalian cells, Anjou65 stable clone, Cos7 stable clone (Cos7-S), and Cos7 transient transfectant (Cos7-T). The transient and stable cloned cells were cultured in 0.5% FCS for 4 days, before harvest. As the maximum yield of mammalian rIL-32β was only 1 ng/ml and IL-32α was below 100 pg/ml concentration, each endotoxin free mammalian rIL-32β was purified using an affinity column prepared by immobilizing an anti-IL-32β mAb to agarose beads (Affi-Gel Hz, Bio-Rad) in the presence of sodium azide (0.2%) to prevent microorganism contamination during purification. The purified rIL-32 was dialyzed against RPMI containing penicillin/streptomycin (10 μg/ml) overnight at 4° C. prior to use for bioassay. All three mammalian rIL-32β preparations induced TNFα in human PMA-differentiated THP-1 cells and in mouse Raw cells, respectively (FIG. 6C). *E. coli* rIL-32α and mammalian rIL-32β increased human TNFα product in PMA differentiated-THP-1 cells in a dose dependent manner (FIG. 6D). Furthermore, the high unit *E. coli* rIL-32α and mammalian Anjou 65 mL-320 preparations induced human IL-8 in undifferentiated-THP-1 cells, whereas the mock Anjou65 transfectants did not (FIG. 6E).

EXAMPLE 9

Production of a Neutralizing Fab Fragment of an Anti-IL-32 Monoclonal Antibody

A five week old female Balb/c mouse was immunized with 20 μg of rIL-32β antigen emulsified in Freund's complete adjuvant (Sigma). On days 14 and 21, the mouse was given an intravenous and intraperitoneal injection with the antigen emulsified in Freund's incomplete adjuvant (Sigma). After three injections, the mouse was sacrificed, the spleen was aseptically harvested, and splenocytes were prepared for fusion. Briefly, $1 \times 10^7$ splenocytes and $1 \times 10^6$ NS-1 mouse myeloma cells (ATCC) were fused using polyethylene glycol 1500 (Roche Applied Science. Indianapolis, Ind.). Fused cells were resuspended at $1 \times 10^6$ cells/ml in hybridoma growth media with 10% FCS and HAT, and plated in 96 well plates. After 2 weeks, the culture supernatants of hybridomas were titrated in an indirect ELISA. Monoclonal antibody classes and subclasses were determined using an IMMUNOTYPE mouse monoclonal antibody isotyping kit (BD Bioscience, San Diego, Calif.) according to the manufacturer's instructions.

Approximately $5 \times 10^6$ cells of two hybridomas 32-4 (IgG$_1$) and 32-9 (IgG$_1$) were intraperitoneally injected into an 8 week old female Balb/c mouse. After one week, ascites fluid was collected using a sterile hypodermic needle. Antibodies from the ascites' supernatant was purified by using a protein A Sepharose column (Bio-Rad), and eluted with 0.1 M glycine-HCl, pH 2.7. The eluted mAbs were dialyzed in PBS, and purified antibodies were concentrated using Centricon concentrators (YM-50, Life Sciences, Ann Arbor, Mich.). The concentration of purified antibody was determined by measuring absorbance at 280 nm.

Figure 7:
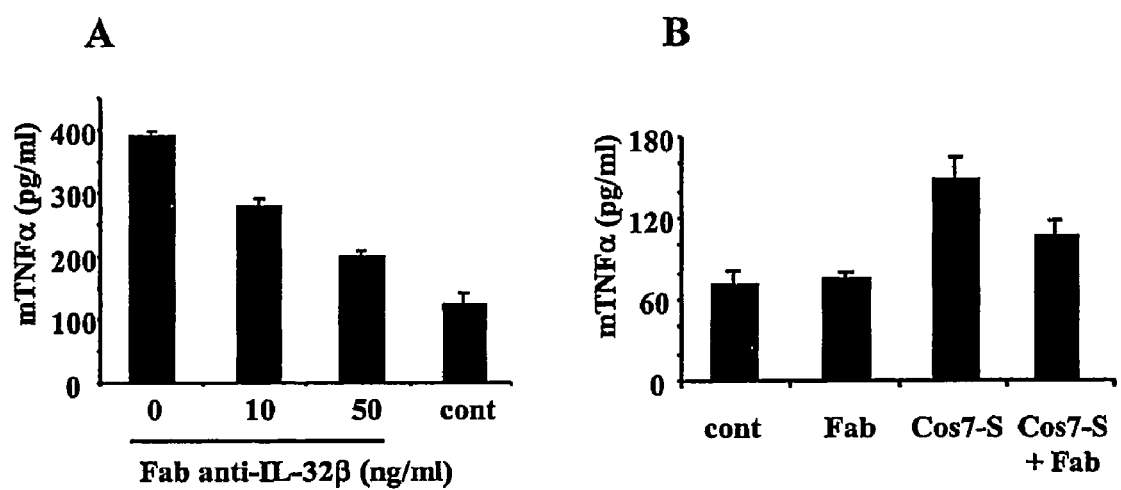
FIG. 7 illustrates that *E. coli* rIL-32α and mammalian rIL-32β activities are neutralized by anti-IL-32 Fab (32-4) treatment (mean±SEM of three separate experiments). Panel A shows the dose dependent reduction in TNFα secretion by mouse Raw cells cultured in the presence of *E. coli* rIL-32α (3 U/ml) and an anti-IL32 Fab. Panel B shows that mammalian (Cos7-S) rIL-32β (2 U/ml) induced mTNFα secretion was inhibited by an anti-IL-32 Fab (40 ng/ml).

As the affinity-purified monoclonal antibody (32-4) against rIL-32β induced a high background level of mTNFα, a Fab fragment of this monoclonal (mAb) was prepared. Briefly, Fab fragments of the purified anti-IL-32 mAb (32-4) were generated by incubating with immobilized-Pepsin (PIERCE, Rockford, Ill.) at 37° C. for 4 h. Fc fragments and residual uncleaved mAbs were removed by using protein G Sepharose (Amersham Biosciences, Uppsla, Sweden). The Fab fragment was dialyzed against PBS overnight at 4° C. and subjected to SDS-PAGE in order to confirm that cleavage was complete. The background level reduced dramatically after removing the Fc fragment, permitting the assessment the IL-32 neutralization activity of the anti-rIL-32β mAb. As shown in FIG. 7A, the Fab of the 32-4 mAb (50 ng/ml) inhibited the biological activity of *E. coli* rIL-32α by more than 70%. As shown in FIG. 7B, the same Fab inhibits the biological activity of the affinity purified Cos7-S rIL-32β by greater than 65%. Higher concentrations of the Fab fragment didn't further inhibit IL-32-induced TNFα production in these assays.

EXAMPLE 10

Therapeutic Effect of IL-32-Antibodies and IL-32 Inhibitors in a Murine Model of Inflammatory Bowel Disease This example provides details of the experiments conducted to assess the effect of IL-32-antibodies and IL-32 antagonists (e.g., soluble IL-32 receptors, dominant-negative IL-32 variants, small molecule inhibitors, etc.) as therapeutics for the treatment of dextran sulphate sodium (DSS)-induced colitis in mice.

Briefly, colitis is induced in 8-10 week old female C57BL/6 mice (Taconic Laboratories) by administering 2% (wt/vol) dextran sodium sulphate (DSS, MW 40,000 from ICN Biochemicals) from day 0 to day 7 in the drinking water ad libitum, followed by return to normal water as known in the art (Sivakumar et al., *Gut*, 50:812-820, 2002). Mice are weighed every day beginning on day 0 and weight changes are recorded until day 13. Percent weight change for each mouse is calculated as follows: percent weight change= (weight on specific day−weight on day 0)/weight on day 0×100. Groups of mice are treated with: a control protein (50 μg or 500 μg); murine anti-IL-32 mAb (50 μg or 500 μg); and recombinant IL-32 antagonist (e.g., IL-32 receptor-IgG1 Fc fusion protein or dominant-negative IL-32 variant, at 50 μg or 500 μg), each in a volume of 200 μl per injection (endotoxin-free PBS). Mice are injected IP from day 0 to day 7. The mice are sacrificed on days 0, 2, 4, 6, or 8 following the start of DSS treatment, by anesthesia and cervical dislocation, and tissues (e.g., large intestine, lymph nodes) are removed and processed for RNA extraction, histopathology and cytokine analysis, using methods known in the art. It is contemplated that administration of IL-32 antagonists is suitable for attenuation of inflammation during DSS induced colitis in mice, and that neutralizing IL-32 activity is of benefit for ameliorating the inflammation associated with intestinal diseases.

EXAMPLE 11

Therapeutic Effect of IL-32-Antibodies and IL-32 Inhibitors in a Murine Model of Hepatitis This example provides details of the experiments conducted to assess the effect of IL-32-antibodies and IL-32 antagonists (e.g., soluble IL-32 receptors, dominant-negative IL-32 variants, small molecule inhibitors, etc.) as therapeutics for the treatment of LPS-induced liver injury in mice primed with heat-killed *Propioibacterium acnes* (model of Fas/FasL-mediated liver disease).

Briefly, hepatitis is induced in 8-10 week old female BALB/c mice (Charles River Laboratories) by administering 500 μg/mouse IV of heat-killed *P. acnes* (Ribi Immuno-Chem Research) and 12 days later they are challenged with 50 μg/kg LPS IV as known in the art (Faggioni et al., *J Immunol*, 167:5913-5920, 2001). Groups of mice are treated with: a control protein (50 μg or 500 μg); murine anti-IL-32 mAb (50 μg or 500 μg); and recombinant IL-32 antagonist (e.g., IL32 receptor-IgG1 Fc fusion protein or dominant-negative IL-32 variant, at 50 μg or 500 μg), each in a volume of 200 μl per injection (endotoxin-free PBS). Mice are injected IP either at the time of *P. acnes* administration or 10 min before LPS challenge. Mice are monitored for survival or sacrificed to collect livers for histological examination, mRNA and chemokine measurements, and blood for serum IFN-γ and transaminase measurements using methods known in the art. It is contemplated that administration of IL-32 antagonists is suitable for preventing LPS-induced liver damage and IFN-γ and Fas ligand expression when administered 10 minutes before LPS challenge pf *P. acnes*-primed mice. In addition, the administration of IL-32 antagonists is contemplated to be suitable for decreasing *P. acnes*-induced granuloma formation, macrophage-inflammatory protein-1α and macrophage-inflammatory protein-2 production, when given at the moment of priming with *P. acnes*. Thus it is contemplated that patients with liver diseases such as HCV-induced hepatitis, autoimmune hepatitis, and primary biliary cirrhosis will benefit from a therapy regimen comprising an IL-32 antagonist.

EXAMPLE 12

Therapeutic Effect of IL-32-Antibodies and IL-32 Inhibitors in a Murine Model of Ischemic Disease This example provides details of the experiments conducted to assess the effect of IL-32-antibodies and IL-32 antagonists (e.g., soluble IL-32 receptors, dominant-negative IL-32 variants, small molecule inhibitors, etc.) as therapeutics for stimulating tissue neovascularization in response to ischemic injury.

Briefly, male C57BL/6J mice undergo surgery to induce unilateral hindlimb ischemia using methods known in the art (Mallat et al., Circ Res, 91:441-448, 2002). Animals are anesthetized by isoflurane inhalation. The ligature is performed on the right femoral artery, 0.5 cm proximal to the bifurcation of the saphenous and popliteal arteries, and then housed under conventional conditions for 3 or 28 days. Groups of mice are treated with: a control protein (50 μg or 500 μg); murine anti-IL-32 mAb (50 μg or 500 μg); and recombinant IL-32 antagonist (e.g., IL-32 receptor-IgG1 Fc fusion protein or dominant-negative IL-32 variant, at 50 μg or 500 μg), each in a volume of 200 μl per injection (endotoxin-free PBS). Mice are injected IP at day 0, and day 7. The degree of angiogenesis is quantified on days 3 and 10, by measuring vessel density by microangiography, and ischemia-induced changes in vascularization is monitored by laser Doppler perfusion imaging. It is contemplated that administration of IL-32 antagonists is suitable for stimulating tissue neovascularization in response to ischemic injury.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in molecular biology, genetics, immunology or related fields are intended to be within the scope of the claims.

We claim:

1. An isolated nucleic acid comprising SEQ ID NO:15.

2. The nucleic acid of claim 1, wherein said nucleic acid comprises SEQ ID NO:3.

3. The nucleic acid of any one of claims 1 or 2, wherein said nucleic acid is operably linked to a heterologous promoter.

4. A vector comprising the nucleic acid of claim 3.

5. A host cell comprising the vector of claim 4.

* * * * *

UNITED STATES PATENT AND TRADEMARK OFFICE
CERTIFICATE OF CORRECTION

| | | |
|---|---|---|
| PATENT NO. | : 7,560,265 B2 | Page 1 of 1 |
| APPLICATION NO. | : 10/578943 | |
| DATED | : July 14, 2009 | |
| INVENTOR(S) | : Kim et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (0) days Delete the phrase "by 0 days" and insert -- by 61 days --

Signed and Sealed this

Ninth Day of February, 2010

David J. Kappos
*Director of the United States Patent and Trademark Office*

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
ctgtcccgag tctggacttt                                                    20

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
gcaaaggtgg tggtcagtat c                                                  21

<210> SEQ ID NO 3
<211> LENGTH: 396
<212> TYPE: DNA
<213> ORGANISM: Homo sapiens

<400> SEQUENCE: 3
atgtgcttcc cgaaggtcct ctctgatgac atgaagaagc tgaaggcccg aatgcaccag         60
gctatagaaa gattttatga taaaatgcaa aatgcagaat caggacgtgg acaggtgatg        120
tcgagcctgg cagagctgga ggacgacttc aaagagggct acctggagac agtggcggct        180
tattatgagg agcagcaccc agagctcact cctctacttg aaaagaaag atgggatta         240
cggtgccgag gcaacagatc ccctgtcccg gatgttgagg atcccgcaac cgaggagcct        300
ggggagagct tttgtgacaa gtcctacgga gccccacggg gggacaagga ggagctgaca        360
ccccagaagt gctctgaacc ccaatcctca aaatga                                  396

<210> SEQ ID NO 4
<211> LENGTH: 567
<212> TYPE: DNA
<213> ORGANISM: Homo sapiens

<400> SEQUENCE: 4
atgtgcttcc cgaaggtcct ctctgatgac atgaagaagc tgaaggcccg aatgcaccag         60
gccatagaaa gattttatga taaaatgcaa aatgcagaat caggacgtgg acaggtgatg        120
tcgagcctgg cagagctgga ggacgacttc aaagagggct acctggagac agtggcggct        180
tattatgagg agcagcaccc agagctcact cctctacttg aaaagaaag atgggatta         240
cggtgccgag gcaacagatc ccctgtcccg gatgttgagg atcccgcaac cgaggagcct        300
ggggagagct tttgtgacaa ggtcatgaga tggttccagg ccatgctgca gcggctgcag        360
acctggtggc acgggttct ggcctgggtg aaggagaagg tggtggccct ggtccatgca        420
gtgcaggccc tctggaaaca gttccagagt ttctgctgct ctctgtcaga gctcttcatg        480
tcctcttttcc agtcctacgg agccccacgg ggggacaagg aggagctgac accccagaag        540
tgctctgaac cccaatcctc aaaatga                                           567

<210> SEQ ID NO 5
<211> LENGTH: 705
<212> TYPE: DNA
<213> ORGANISM: Homo sapiens

<400> SEQUENCE: 5

```
atgtgcttcc cgaaggtcct ctctgatgac atgaagaagc tgaaggcccg aatggtaatg      60
ctcctcccta cttctgctca gggggttgggg gcctgggtct cagcgtgtga cactgaggac     120
actgtgggac acctgggacc ctggagggac aaggatccgg ccctttggtg ccaactctgc     180
ctctcttcac agcaccaggc catagaaaga ttttatgata aaatgcaaaa tgcagaatca     240
ggacgtggac aggtgatgtc gagcctggca gagctggagg acgacttcaa agagggctac     300
ctggagacag tggcggctta ttatgaggag cagcacccag agctcactcc tctacttgaa     360
aaagaaagag atggattacg gtgccgaggc aacagatccc ctgtcccgga tgttgaggat     420
cccgcaaccg aggagcctgg ggagagcttt tgtgacaagg tcatgagatg gttccaggcc     480
atgctgcagc ggctgcagac ctggtggcac ggggttctgg cctgggtgaa ggagaaggtg     540
gtggccctgg tccatgcagt gcaggccctc tggaaacagt tccagagttt ctgctgctct     600
ctgtcagagc tcttcatgtc ctctttccag tcctacggag ccccacgggg ggacaaggag     660
gagctgacac cccagaagtg ctctgaaccc caatcctcaa aatga                     705
```

<210> SEQ ID NO 6
<211> LENGTH: 537
<212> TYPE: DNA
<213> ORGANISM: Homo sapiens

<400> SEQUENCE: 6

```
atgaagaagc tgaaggcccg aatgcaccag gccatagaaa gattttatga taaaatgcaa      60
aatgcagaat caggacgtgg acaggtgatg tcgagcctgg cagagctgga ggacgacttc     120
aaagagggct acctggagac agtggcggct tattatgagg agcagcaccc agagctcact     180
cctctacttg aaaaagaaag gatggattac ggtgccgag gcaacagatc ccctgtcccg     240
gatgttgagg atcccgcaac cgaggagcct ggggagagct tttgtgacaa ggtcatgaga     300
tggttccagg ccatgctgca gcggctgcag acctggtggc acggggttct ggcctgggtg     360
aaggagaagg tggtggccct ggtccatgca gtgcaggccc tctggaaaca gttccagagt     420
ttctgctgct ctctgtcaga gctcttcatg tcctctttcc agtcctacgg agccccacgg     480
ggggacaagg aggagctgac accccagaag tgctctgaac cccaatcctc aaaatga      537
```

<210> SEQ ID NO 7
<211> LENGTH: 131
<212> TYPE: PRT
<213> ORGANISM: Homo sapiens

<400> SEQUENCE: 7

Met Cys Phe Pro Lys Val Leu Ser Asp Asp Met Lys Lys Leu Lys Ala
1               5                  10                  15

Arg Met His Gln Ala Ile Glu Arg Phe Tyr Asp Lys Met Gln Asn Ala
            20                  25                  30

Glu Ser Gly Arg Gly Gln Val Met Ser Ser Leu Ala Glu Leu Glu Asp
        35                  40                  45

Asp Phe Lys Glu Gly Tyr Leu Glu Thr Val Ala Ala Tyr Tyr Glu Glu
    50                  55                  60

Gln His Pro Glu Leu Thr Pro Leu Leu Glu Lys Glu Arg Asp Gly Leu

```
                65                  70                  75                  80
Arg Cys Arg Gly Asn Arg Ser Pro Val Pro Asp Val Glu Asp Pro Ala
                    85                  90                  95

Thr Glu Glu Pro Gly Glu Ser Phe Cys Asp Lys Ser Tyr Gly Ala Pro
            100                 105                 110

Arg Gly Asp Lys Glu Glu Leu Thr Pro Gln Lys Cys Ser Glu Pro Gln
        115                 120                 125

Ser Ser Lys
    130

<210> SEQ ID NO 8
<211> LENGTH: 188
<212> TYPE: PRT
<213> ORGANISM: Homo sapiens

<400> SEQUENCE: 8

Met Cys Phe Pro Lys Val Leu Ser Asp Asp Met Lys Lys Leu Lys Ala
1               5                   10                  15

Arg Met His Gln Ala Ile Glu Arg Phe Tyr Asp Lys Met Gln Asn Ala
            20                  25                  30

Glu Ser Gly Arg Gly Gln Val Met Ser Ser Leu Ala Glu Leu Glu Asp
        35                  40                  45

Asp Phe Lys Glu Gly Tyr Leu Glu Thr Val Ala Ala Tyr Tyr Glu Glu
    50                  55                  60

Gln His Pro Glu Leu Thr Pro Leu Leu Glu Lys Glu Arg Asp Gly Leu
65                  70                  75                  80

Arg Cys Arg Gly Asn Arg Ser Pro Val Pro Asp Val Glu Asp Pro Ala
                    85                  90                  95

Thr Glu Glu Pro Gly Glu Ser Phe Cys Asp Lys Val Met Arg Trp Phe
            100                 105                 110

Gln Ala Met Leu Gln Arg Leu Gln Thr Trp Trp His Gly Val Leu Ala
        115                 120                 125

Trp Val Lys Glu Lys Val Val Ala Leu Val His Ala Val Gln Ala Leu
    130                 135                 140

Trp Lys Gln Phe Gln Ser Phe Cys Cys Ser Leu Ser Glu Leu Phe Met
145                 150                 155                 160

Ser Ser Phe Gln Ser Tyr Gly Ala Pro Arg Gly Asp Lys Glu Glu Leu
                165                 170                 175

Thr Pro Gln Lys Cys Ser Glu Pro Gln Ser Ser Lys
            180                 185

<210> SEQ ID NO 9
<211> LENGTH: 234
<212> TYPE: PRT
<213> ORGANISM: Homo sapiens

<400> SEQUENCE: 9

Met Cys Phe Pro Lys Val Leu Ser Asp Asp Met Lys Lys Leu Lys Ala
1               5                   10                  15

Arg Met Val Met Leu Leu Pro Thr Ser Ala Gln Gly Leu Gly Ala Trp
            20                  25                  30

Val Ser Ala Cys Asp Thr Glu Asp Thr Val Gly His Leu Gly Pro Trp
        35                  40                  45

Arg Asp Lys Asp Pro Ala Leu Trp Cys Gln Leu Cys Leu Ser Ser Gln
    50                  55                  60

His Gln Ala Ile Glu Arg Phe Tyr Asp Lys Met Gln Asn Ala Glu Ser
```

```
                65                  70                  75                  80
Gly Arg Gly Gln Val Met Ser Ser Leu Ala Glu Leu Glu Asp Asp Phe
                    85                  90                  95

Lys Glu Gly Tyr Leu Glu Thr Val Ala Ala Tyr Tyr Glu Glu Gln His
                100                 105                 110

Pro Glu Leu Thr Pro Leu Leu Glu Lys Glu Arg Asp Gly Leu Arg Cys
                115                 120                 125

Arg Gly Asn Arg Ser Pro Val Pro Asp Val Glu Asp Pro Ala Thr Glu
            130                 135                 140

Glu Pro Gly Glu Ser Phe Cys Asp Lys Val Met Arg Trp Phe Gln Ala
145                 150                 155                 160

Met Leu Gln Arg Leu Gln Thr Trp Trp His Gly Val Leu Ala Trp Val
                165                 170                 175

Lys Glu Lys Val Val Ala Leu Val His Ala Val Gln Ala Leu Trp Lys
                180                 185                 190

Gln Phe Gln Ser Phe Cys Cys Ser Leu Ser Glu Leu Phe Met Ser Ser
                195                 200                 205

Phe Gln Ser Tyr Gly Ala Pro Arg Gly Asp Lys Glu Glu Leu Thr Pro
            210                 215                 220

Gln Lys Cys Ser Glu Pro Gln Ser Ser Lys
225                 230

<210> SEQ ID NO 10
<211> LENGTH: 178
<212> TYPE: PRT
<213> ORGANISM: Homo sapiens

<400> SEQUENCE: 10

Met Lys Lys Leu Lys Ala Arg Met His Gln Ala Ile Glu Arg Phe Tyr
1               5                   10                  15

Asp Lys Met Gln Asn Ala Glu Ser Gly Arg Gly Gln Val Met Ser Ser
                20                  25                  30

Leu Ala Glu Leu Glu Asp Asp Phe Lys Glu Gly Tyr Leu Glu Thr Val
            35                  40                  45

Ala Ala Tyr Tyr Glu Glu Gln His Pro Glu Leu Thr Pro Leu Leu Glu
        50                  55                  60

Lys Glu Arg Asp Gly Leu Arg Cys Arg Gly Asn Arg Ser Pro Val Pro
65                  70                  75                  80

Asp Val Glu Asp Pro Ala Thr Glu Glu Pro Gly Glu Ser Phe Cys Asp
                85                  90                  95

Lys Val Met Arg Trp Phe Gln Ala Met Leu Gln Arg Leu Gln Thr Trp
                100                 105                 110

Trp His Gly Val Leu Ala Trp Val Lys Glu Lys Val Val Ala Leu Val
            115                 120                 125

His Ala Val Gln Ala Leu Trp Lys Gln Phe Gln Ser Phe Cys Cys Ser
        130                 135                 140

Leu Ser Glu Leu Phe Met Ser Ser Phe Gln Ser Tyr Gly Ala Pro Arg
145                 150                 155                 160

Gly Asp Lys Glu Glu Leu Thr Pro Gln Lys Cys Ser Glu Pro Gln Ser
                165                 170                 175

Ser Lys

<210> SEQ ID NO 11
<211> LENGTH: 5000
<212> TYPE: DNA
```

<213> ORGANISM: Homo sapiens

<400> SEQUENCE: 11

```
gcctagggtg gaccctattt caatatgact ggtgtccttt ggaaagggga aaggggaca      60
gtcacaccca ggcagaacgt gatgaagatg aagatggcca tctacaaggg caggagaaac    120
ctgaacagaa tcccagctcc gggccctcag aaggacccca cgctgcccac attgaccttg    180
gacctccagc ctgcagatcg tgagggaaga gacgtcttcg acttagggcc ccttgtcgtg    240
gtacttcctt agtttggccc caggaaacca tcccaaaggc aagggcgtgg ttgtgctcag    300
ctggggggaag gggctgggg gccgtgagga ggaggtggga ggcccagcca ggctggaggg    360
tcagaacccg tggagctaga agagcccgta ggggagcccc aagattgctg agaccagtga    420
ccttcggccc cagatggcct tgccttggcc cagaagggtc agaaggacct ggtcagccaa    480
gctcagacag ccggcaggat gccttccacc ctgcagaggg tcctatcttg tcccacaggt    540
agatctacat caccactagc caccccctcca acgtgcacag gccctgccc tcacggcgcc    600
cctcttaggt ccggcagttc ctgcctcctt ctgatccaga gtttctctg gcctctggag    660
ccggggcaca cctcatgcaa ggacagggtc caaattcctt tgtccttgga tcccacttgg    720
ctgacgtcac cttcctgtac tcagggagtt tccccagcca gctgtcccga gtctggactt    780
tccctctgcc cctccccact tcaggctgg tggggtgggg aaagcagccc attcctgggc    840
tcagagactc ccaccccagc tcagagggag caggggccca gccagggacg gaccctcatt    900
cctcccaggg accccagacc tctgtctctc tcgggtaagt ctccatctct gtctgtctct    960
gtctctgtct ctgtctctgt ctgttttttca cgcactcagc aaggcctcct gccctgagag   1020
aggctccgcc cactaccccc cactttcccc ataaaaccag ctgagtattt gtgccaggaa   1080
gactgcgtgc agaaggtgac tgtctcagtg gagctgggtc atctcaggtg gggagttggg   1140
gtccccgaag gtgaggaccc tctggggagg agggtgcttc tctgagacac ttctttccc   1200
tcacacctgt tcctcgccag caggccttgg ctccttgaac ttttggccgc catgtgcttc   1260
ccgaaggtga gtgagaggct gcgtgtgctt ttgtgggcat gtctgaaaac agaccgtaag   1320
ggtgcgggtg ccctcagtat ttccccgaggt gcctgtgtgt cagggctcag tcaggggcac   1380
ccagcggcag gaggatagtg atggggtgag agtgtcagtg gaggcgctgg aggtcatatg   1440
tgtcggggggc gctggagaac ggcaggggtg tggatgagag ggagcacctg tcccaggagc   1500
ccttcacagc ccggaaagcc cggggcaggg gtggggcagg gctctgctgg aaacgactcg   1560
gagaatgctt ctctcagagg ccggctcagc tgggtgggcc caagagcaag gctgtgtgg   1620
gtcctggtgt ctcttcctcc tttcctgggt tccctccgac ctcccatcct ctaccactgc   1680
cccaccgcaa atgctaggcc caccacaccc tccagggagc tcttcggcct gtgacaatag   1740
gggtttccat gatgtggcct ggctcaggtt caggacagtg acccggagga cacatggctc   1800
ccgcatgtcg gcacggtgct gctttcaccc tggttcctgg gaaatcaggc tagcgggatg   1860
ggaccatcgc tgcctgaaag tgtgcagaca gctgccctgc ccagaatatg tccccaggcc   1920
ctgcgcactc tgtgggtgac tgtcaccact ctatagtggg ggaaaccagg catgtcaccc   1980
ccgagactag gcccttgacg tgggggctca gcggggattc tgtggggtgc ctctggcctc   2040
tgtggatgca gccacgtgtc tgcaggcagg aatggcccgg gacctgtggg tctgcatgtt   2100
ggcagtcggg aagagtggca ggttgtaggg tggacctacc tggcacccca aatattaatc   2160
agctcatcag agaggaatgg ctgctgttac cttctcaatt gtcatgtccc taaacatttt   2220
ttccttggcc aactctcacc tgggaccata gtggttgtgg gaaacccagc tgagccagcc   2280
```

```
tgctccagga cagtgtccat cctcccgtgt gtgtacatgg gggggtgtgt gtgtgcaggg    2340
aggacacccc ggcccacgca ggccctgctc ttgtgaggag gggtcaccta ggcccacgca    2400
ggccctgctc ttgtgaggag gggtcaccta ggcccacgca ggccctgctc ttgtgaggag    2460
gggtcaccta ggcccacgca ggccctgctc ttgtgaggag gggtcaccta ggcccacgca    2520
ggccctgctc ttgtgaggag gggtcaccta ggcccatgct ggccctgctc ttgggcctgc    2580
ccagctgagc cggctcctga gagaagcgct ttctgagtcg tttcgaggac agccctggcc    2640 ggtcttttcca ggctgtgagg ggctcctggg actgctgtct cctcttatcc tgtacctctg    2700
ccatgtgtct ctgtgtgtgt gtgtgtgtgt gtgtgtgtgt gtgtgtgtgt ataaattatc    2760
ctggaggaaa ggttaaggtg acacatggag actgagtgtc accgttattt ccgcaggtcc    2820
tctctgatga catgaagaag ctgaaggccc gaatggtaat gctcctccct acttctgctc    2880
aggggttggg ggcctgggtc tcagcgtgtg acactgagga cactgtggga cacctgggac    2940
cctggaggga caaggatccg gccctttggt gccaactctg cctctcttca cagcaccagg    3000
ccatagaaag attttatgat aaaatgcaaa atgcagaatc aggacgtgga caggtgggtg    3060
gatttcccct caggcaccag gtcacatgtc cccgccccca ggcactccac cctgtgtggg    3120
gctcagggtg agaaggatga agagggaccc acaggctccc tcacccctta ccgtgggcaa    3180
atgcttgcac ctgggtggca gtgagtgggc gggtggggga tctggacgcc cggggagact    3240
gagggaggca tccaagcccc agggctcctt gaggaaacaa cagggtgcc agacgtggcc      3300 cgggcccctg gctgggccca gttcggggtg tgtgggagct gaggactcac tgggcttgag    3360
gactgactga tgtggggtgc agaggaggct tgggcctgga accgagtgct ttgttcctaa    3420
caggtgatgt cgagcctggc agagctggag gtgagccgtg gcctccccct ccaccaagct    3480
tagtccctgg gtcttaggct ccacaggaca ctgggtctgg gccccgggtc cccttgggaa    3540
tcacctggac cagtggggggc cacagtggga agggggcagg caggagcagc atgaaccccc    3600
tgtgccctcc tctccccagg acgacttcaa agagggctac ctggagacag tggcggctta    3660
ttatgaggag cagcacccag tgagtatgac acacccatct gggcaccttg ccttccttca    3720
cctctgccct gtcttttctt tctttctttc tttttgttta tttgagacag agtctcgctc    3780
tgtcgcccag gctggagtgc agtggcatga tcttggctca ctgcaacctc caaatctcgg    3840
gtttaagtga ttctcctgcc tcagcctgac aagtagttgg gactacaggc acccgccacc    3900
actccaggct gatttttttt gtgtgtgttt ttagtagaga ccaggtttca ccatgtttgc    3960
caggctggtc ttgaactcct aaccttgtgt tccgtctgcc ttggcctccc aaagtgctga    4020
gattacaggc atgagccacc gggcccagcc aaccctgcc ctgtcttgat gtggtgtggg     4080
cagggtgtgc ccagcccctg agcttgggt ggagggctgg gagtgacagc tagctggga      4140 cctgcccatg gcctcactcc tcacacagtg gcacagccct caaggcacga tgagggccct    4200
gacctggtga ccaagcagac acacccatcc tgtcactgcc atggaggtga atgcagagga    4260
gggggactct gggaaaagtc cctcttgccc acgggctgt ggttgggaaa ccaacacctg      4320
tgggcctccg tctcccaggg tcaggaaaag gctgagaggc ctgggtgtgg ccagggcctg    4380
gggctgacac ccccacctac agaccctgaa tggtgctccc attccacagg agctcactcc    4440
tctacttgaa aaagaaagag atggattacg gtgccgaggc aacagatccc ctgtcccgga    4500
tgttgaggat cccgcaaccg aggagcctgg ggagagcttt tgtgacaagg tcatgagatg    4560
gttccaggcc atgctgcagc ggctgcagac ctggtggcac ggggttctgg cctgggtgaa    4620
```

```
ggagaaggtg gtggccctgg tccatgcagt gcaggccctc tggaaacagt tccagagttt    4680
ctgctgctct ctgtcagagc tcttcatgtc ctctttccag tcctacggag ccccacgggg    4740
ggacaaggag gagctgacac cccagaagtg ctctgaaccc caatcctcaa aatgaagata    4800
ctgacaccac ctttgccctc cccgtcaccg cgcacccacc ctgacccctc cctcagctgt    4860
cctgtgcccc gccctctccc gcacactcag tcccctgcc tggcgttcct gccgcagctc     4920
tgacctggtg ctgtcgccct ggcatcttaa taaaacctgc ttatacttcc ctggcagggg    4980
agataccatg atcgcggagg                                                5000

<210> SEQ ID NO 12
<211> LENGTH: 285
<212> TYPE: DNA
<213> ORGANISM: Mus musculus

<400> SEQUENCE: 12
accgtcacat tgcccaacac ttgcttacaa atctagaact cttgttttgc aacctgccaa      60
ccttcttttt tgcttcccct gttttttctc ctaggaagtg tgttaagaca gtaccctgt     120 atacttacct ggcaggggag ataccatgat cacgaaggtg gttttcccag ggcgaggctt    180
atccattgca ctccggatgt gctgacccct gcgatttccc caaatgcggg aaactcgact    240
gcataatttg tggtagtggg ggactgcgtt cccgctctcc cctgg                    285

<210> SEQ ID NO 13
<211> LENGTH: 26
<212> TYPE: PRT
<213> ORGANISM: Homo sapiens

<400> SEQUENCE: 13

Leu Lys Ala Arg Met His Gln Ala Ile Glu Arg Phe Tyr Asp Lys Met
1               5                   10                  15

Gln Asn Ala Glu Ser Gly Arg Gly Gln Val
            20                  25

<210> SEQ ID NO 14
<211> LENGTH: 46
<212> TYPE: PRT
<213> ORGANISM: Homo sapiens

<400> SEQUENCE: 14

Val Met Leu Leu Pro Thr Ser Ala Gln Gly Leu Gly Ala Trp Val Ser
1               5                   10                  15

Ala Cys Asp Thr Glu Asp Thr Val Gly His Leu Gly Pro Trp Arg Asp
            20                  25                  30

Lys Asp Pro Ala Leu Trp Cys Gln Leu Cys Leu Ser Ser Gln
        35                  40                  45

<210> SEQ ID NO 15
<211> LENGTH: 108
<212> TYPE: DNA
<213> ORGANISM: Homo sapiens

<400> SEQUENCE: 15
ccgaaggtcc tctctgatga catgaagaag ctgaaggccc gaatgcacca ggctatagaa     60
agattttatg ataaaatgca aaatgcagaa tcaggacgtg gacaggtg                 108

<210> SEQ ID NO 16
<211> LENGTH: 179
<212> TYPE: PRT
```

<213> ORGANISM: Equus caballus

<400> SEQUENCE: 16

Met Gly Tyr Pro Lys Thr Ser Arg Glu Asp Asn Glu Arg Trp Lys Ile
1               5                   10                  15

Arg Phe His Ser Thr Leu Asp Arg Trp Leu Asp Asp Ile Glu Val Gln
            20                  25                  30

Ser Gln Gly Glu Glu Gln Val Asp Leu Gly Leu Glu Asp Leu Glu Glu
        35                  40                  45

Lys Phe Ser Glu Asn Ile Leu Asp Ala Val Glu Glu His His Gln Lys
50                  55                  60

Asn Asn Ser Glu Ser Ala Pro Leu Leu Pro Asp Val Lys Pro Arg Leu
65                  70                  75                  80

Arg Arg Arg Ala Gln Lys Ser Ser Val Leu Asn Pro Glu Pro Glu Gly
                85                  90                  95

Pro Gly Ile Leu Gln Val Glu Ala Leu Glu Ala Pro Glu Pro Glu Glu
            100                 105                 110

Ser Phe Trp Val Arg Ala Trp Arg Ser Phe Met Gly Met Leu Gln Arg
        115                 120                 125

Leu Lys Gln Arg Trp Gln Ala Val Leu Ala Trp Val Arg Glu Lys Val
130                 135                 140

Ala Ala Gly Trp Gln Ala Leu Cys Ser Val Ala Gln Ser Ile Asn Ser
145                 150                 155                 160

Val Leu Glu Ser Phe Cys Ser Tyr Met Ala Gly Leu Phe Arg Tyr His
                165                 170                 175

Ile Gln Val

<210> SEQ ID NO 17
<211> LENGTH: 170
<212> TYPE: PRT
<213> ORGANISM: Bos taurus

<400> SEQUENCE: 17

Met Cys Phe Ala Lys Gly Val Pro Tyr Asp Gln Ala Ser Leu Arg Ser
1               5                   10                  15

Ile Met His Lys Arg Val Asp Asp Phe Cys Asp Lys Met Gly Asn Glu
            20                  25                  30

Pro Glu Glu Ala Gln Met Glu Ala Ala Leu Asp Glu Thr Glu Glu Gly
        35                  40                  45

Leu Ser Glu Asp Ile Cys Glu Phe Ile Glu Asp His Ile Gln Glu Asn
    50                  55                  60

Leu Pro Glu Ser Leu Gln Glu Ser Ser Pro Leu Leu Gln Glu Ala Arg
65                  70                  75                  80

Gln Gly Val Arg Arg Arg Ile Gln Arg Pro Ser Val Ser Ala Arg Leu
                85                  90                  95

Glu Val Gln Asn Pro Glu Ser Ile Trp Ala Arg Ala Leu Gly Arg
            100                 105                 110

Phe Gln Val Ile Leu Gln Ser Leu Gln Gln Arg Cys Trp Asp Ala Leu
        115                 120                 125

Thr Trp Leu Arg Glu Lys Ala Val Thr Phe Leu Glu Ala Ile Cys Ser
130                 135                 140

Val Val Lys Ala Val Leu Gly Val Leu Thr Asp Phe Cys Ser Ser Val
145                 150                 155                 160

Gly Gln Leu Phe Gly Asn Leu Ile Gln Val
                165                 170

<210> SEQ ID NO 18
<211> LENGTH: 125
<212> TYPE: PRT
<213> ORGANISM: Equus caballus

<400> SEQUENCE: 18

Met Gly Tyr Pro Lys Thr Ser Arg Glu Asp Asn Glu Arg Trp Lys Ile
1               5                   10                  15
Arg Phe His Ser Thr Leu Asp Arg Trp Leu Asp Asp Ile Glu Val Gln
            20                  25                  30
Ser Gln Gly Glu Glu Gln Val Cys Gln Cys Ala Pro Thr Pro Cys Ser
        35                  40                  45
Arg Asn Leu Gly Gly Arg Val Val Thr Met Thr Met Arg Arg Lys Asn
    50                  55                  60
Val Pro Pro Gln Val Asp Leu Gly Pro Leu Thr Ser Pro Phe Ser Gln
65                  70                  75                  80
Arg Thr Phe Arg Ser Asp Leu Cys His Leu Pro Thr Leu Asp Leu Ser
                85                  90                  95
Leu Thr Thr Ser Leu Thr Ser Leu Leu Cys Thr Ala Trp Pro Pro Cys
            100                 105                 110
Pro Pro Cys Thr Ser Cys Ser Gly Phe Leu Leu Gln Val
        115                 120                 125

<210> SEQ ID NO 19
<211> LENGTH: 482
<212> TYPE: DNA
<213> ORGANISM: Equus caballus

<400> SEQUENCE: 19
gcacgagctc gtgccgtgtg ctgagaggcc cttggggcag gcacagcccc tggaatcctg      60
agctgccatg ggctacccca agacgtccag agaagacaat gaacgttgga agatccgatt    120
tcacagcact ttagaccggt ggcttgatga tatcgaagtt caatcccaag agaggaaca     180
ggtgtgtcag tgtgctccca cgccctgctc ccgtaacctc ggggtcggg tggtcacgat     240
gacgatgagg aggaagaacg tgccacctca ggtcgattta ggccctttga cgtccccctt    300
ttcacagaga accttcagaa gtgacctttg ccacctgcct acccttgacc tgtccttgac    360
cacctccctc acctccttgc tgtgcacagc ctggccaccc tgcccaccat gcacttcctg    420
ctcaggtttc cttctgcagg tctgacttgt ggctccagcg catatgtctt aataaagttg    480
tg                                                                    482

<210> SEQ ID NO 20
<211> LENGTH: 815
<212> TYPE: DNA
<213> ORGANISM: Equus caballus

<400> SEQUENCE: 20
ctgagaggcc cttggggcag gcacagcccc tggaatcctg agctgccatg ggctacccca      60
agacgtccag agaagacaat gaacgttgga agatccgatt tcacagcact ttagaccggt    120
ggcttgatga tatcgaagtt caatcccaag agaggaaca ggtcgattta ggcctagaag      180
acctggagga aaaattcagt gaaaacattc ttgacgccgt ggaggagcac catcagaaga    240
acaactcaga atctgcgcct ttacttcctg acgtgaagcc caggttacgt cgcagagctc    300
agaagtcctc tgtcctcaac cctgaacctg agggtccagg gatcctgcaa gttgaggctc    360

-continued

```
tagaggcacc cgagcctgaa gaaagctttt gggtcagagc atggaggtcg ttcatgggga      420
tgctacagcg actgaagcag aggtggcagg ctgtactggc ctgggtgcga gagaaggtgg      480
ctgctggctg caggcccta tgcagtgtgg cccagtccat aatagtgtg cttgagagtt        540 tctgctccta tatggctggg ttgtttaggt accacatcca ggtctagggg gccccatggg      600
gtccaggagg ggtagccaca ccttgcagcc ctttgacgtc cccttttca cagagaacct       660 tcagaagtga cctttgccac ctgcctaccc ttgacctgtc cttgaccacc tcctcacct      720 ccttgctgtg cacagcctgg ccaccctgcc caccatgcac ttcctgctca ggtttccttc      780
tgcaggtctg acttgtggct ccagcgcata gtctt                                 815
```

<210> SEQ ID NO 21
<211> LENGTH: 724
<212> TYPE: DNA
<213> ORGANISM: Bos taurus

<400> SEQUENCE: 21

```
cggattcccg ggatgctcag ctggagctct ggctgcagga tctcaggtcc cttcgggagg       60
accctaagcc accatgtgct tcgctaaggg agtcccatat gaccaggctt ctctgaggtc      120
cataatgcac aaacgggtgg atgatttctg tgataagatg ggaaatgaac cagaagaagc     180
acagatggag gcagccctag atgagacgga ggagggactc agcgaggaca tctgtgaatt     240
catagaagat cacattcaag agaaccttcc cgaatccctg caggagtcca gtcccttgct    300
tcaggaagca cggcaaggag tacgccgcag aatccagaga ccttcagtct ctgcccgtct    360
ggaggtccag aatccggaag agagcatctg gccagagcc ctggggaggt tccaagtaat    420
tctgcagagt ctccagcagc ggtgttggga tgcgctcacc tggctgcggg agaaggcggt    480
gaccttcctg gaggccatct gcagtgtggt gaaggccgtc ttgggagtgc tgacggattt    540
ctgctcctct gtggggcagc tcttcggaaa cctcatccag gtctaggagc cgcaggtggt    600
tctggaggaa ctcctcctca tctaggaggc cctgcaccat cccttccca gaaaccatct    660 tgtgaagcga cctttgcact cctgctcacc cttgacccat cctttaactg ccctcacctc   720
ctgt                                                                  724
```

<210> SEQ ID NO 22
<211> LENGTH: 218
<212> TYPE: PRT
<213> ORGANISM: Bos taurus

<400> SEQUENCE: 22

```
Met Cys Phe Thr Lys Arg Asp Pro Arg Val Leu Ala Ser Phe Arg Val
1               5                   10                  15

Leu Met Val Arg Ser Ser Phe Pro Arg Ile Ala Gly Val Arg Glu Ala
            20                  25                  30

Trp Val Leu Leu Gly Glu Ala Glu Asn Ile Leu Ala His Leu Gly Pro
        35                  40                  45

Ser Arg Glu Lys Asn Arg Asp Ser Phe Thr Gln Val His Leu Cys Ser
    50                  55                  60

Gln His Asn Leu Val Asp Glu Phe Phe Asp Thr Met Glu Asn Glu Pro
65                  70                  75                  80

Glu Gly Ala Gln Met Glu Ala Val Leu Ala Glu Thr Lys Glu Lys Phe
                85                  90                  95

Ile Lys Asp Ala Phe Lys Val Met Asp Asn His Ile Gln Glu Asn Ser
            100                 105                 110
```

```
Pro Glu Thr Leu Lys Glu Ser Ser Pro Leu Leu Gln Glu Ala Arg Gln
        115                 120                 125

Glu Val Arg Cys Arg Ile Gln Arg Arg Ser Val Ser Thr Ser Leu Glu
        130                 135                 140

Val Gln Asn Pro Glu Ser Ile Trp Ala Arg Ala Leu Arg Gln Phe
145                 150                 155                 160

Leu Gly Ile Leu Gln Ser Phe Leu Ser Gly Cys Arg Asp Ala Leu Thr
            165                 170                 175

Trp Leu Trp Glu Lys Ala Ala Cys Leu Gln Ala Ile Cys Ser Ala
            180                 185                 190

Val Glu Ala Leu Trp Glu Val Leu Thr Asp Phe Cys Ser Phe Val Gly
            195                 200                 205

Gln Leu Leu Cys Arg Ser Leu Ile Gln Val
        210                 215

<210> SEQ ID NO 23
<211> LENGTH: 863
<212> TYPE: DNA
<213> ORGANISM: Bos taurus

<400> SEQUENCE: 23
cgggatctca gctggagctc tggctgcagg atctcaggtc ccagcggcag gaccctaagc     60
caccatgtgc ttcactaaga gagacccacg tgtcctggct tctttcaggg tgttaatggt    120
aagaagctca tttccacgta tagctggggt tcgggaggcc tgggttctgc tgggtgaagc    180
tgagaacatt ctggcccact tgggacccag cagggagaag aaccgagatt cttttactca    240
agtccatctc tgttcacagc acaaccttgt agatgaattt ttcgatacaa tggaaaatga    300
accagaagga gcacagatgg aggcagtcct agcagagact aaggagaaat tcatcaagga    360
cgcctttaaa gtcatggata atcacattca agagaacagt cccgaaaccc tgaaggagtc    420
cagtcccttg cttcaggaag cacggcaaga agtacgctgc agaatccaga gacgctccgt    480
ctccacctct ctggaggtcc agaatccgga gagagcatc tgggccagag ccctgcggca    540
gttcttgggc attctgcaga gtttcctgtc cgggtgtcgg gatgcgctca cctggctgtg    600
ggagaaggcc gcggcctgcc tacaggccat ctgcagtgcg gtggaggccc tctgggaagt    660
gctcacggat ttctgctcct tgttgggca gctcttatgc agaagcctca tccaggtcta    720
agagcctcac atggttctgg aggagcccca cctcattcag aaggccctgt acgatgccct    780
tcccggaaac catcttctga agcgaccttt accctcctgc tcacccttga cccatccttt    840
aactgccctc ccctcctgtc ctg                                            863

<210> SEQ ID NO 24
<211> LENGTH: 127
<212> TYPE: PRT
<213> ORGANISM: Ovis aries

<400> SEQUENCE: 24

Met Cys Phe Ala Arg Gly Val Pro His Asp Gln Ala Ser Leu Arg Ser
1               5                   10                  15

Met Leu His Thr Trp Val Asp His Val Cys Asp Lys Met Gly Asn Glu
            20                  25                  30

Pro Glu Glu Ala Gln Met Glu Ala Ala Leu Ala Glu Met Glu Glu Glu
        35                  40                  45

Leu Ser Lys Asp Val Cys Glu Ser Trp Lys Ile Thr Phe Lys Arg Thr
    50                  55                  60
```

```
Phe Pro Asn Pro Cys Arg Ser Pro Val Pro Cys Phe Arg Lys Arg Ser
 65                  70                  75                  80

Lys Lys Tyr Ala Ala Glu Ser Arg Asp Pro Gln Ser Leu Pro Val Trp
                 85                  90                  95

Arg Thr Arg Asn Arg Lys Arg Ala Ser Gly Pro Glu Pro Cys Gly Gly
            100                 105                 110

Ser Glu Val Phe Cys Gly Val Ser Gly Ser Gly Val Ala Met Tyr
        115                 120                 125
```

<210> SEQ ID NO 25
<211> LENGTH: 811
<212> TYPE: DNA
<213> ORGANISM: Ovis aries

<400> SEQUENCE: 25

```
ctgcggtacc ggtccggatt cccgggcgag acagtgctca gctggagctc tggctgcagg      60
atctcagatc ccagccggag gaccctaatc caccatgtgc ttcgctaggg gagtcccaca     120
tgaccaggct tctctgagga gcatgctgca cacctgggtg gatcatgtct gtgataagat     180
gggaaatgaa ccagaagaag cacagatgga ggcagcccta gcagagatgg aggaggaact     240
cagcaaggat gtctgtgaat catggaagat cacattcaag agaaccttcc cgaatccctg     300
caggagtcca gtcccttgct tcaggaagcg cagcaagaag tacgccgcag aatcccgaga     360
ccctcagtct ctgcctgtct ggaggaccag aaaccggaag agagcatctg gccagagcc      420
ctgcggcggt tccgaggttt tctgcggagt ctctggcagc ggtgttgcga tgtactgacc     480
tggctgcagg agaaggcggc ggcctgcctg gaggccgtct gcagtgcggt gaagaccatc     540
tggggagtgc tgacggattt ctgctcctct gtggggcagc tcttcagaaa cctcatccag     600
gtctaggagc cccaggtcgt tcttgaggaa ctgctcctca tctagaaggc cctgcacaat     660
ccccttccca gaaaccatct tctgaagcga cctttaccct cctgttcacc cttcaccaat     720
cctttaactg ccctcacctc ctgtctgcag ggacgacacc acaacatcaa gccaggtttc     780
ccttctccaa gtctgacccg tctgtcaggg a                                    811
```

<210> SEQ ID NO 26
<211> LENGTH: 141
<212> TYPE: PRT
<213> ORGANISM: Sus scrofa

<400> SEQUENCE: 26

```
Met Arg Gly Val Ser Ala Thr Arg Thr Leu Pro Lys Ala Gly Pro Gln
  1               5                  10                  15

Pro Arg Ser Gly Leu Gly Leu Pro Leu Pro Arg Arg Val Pro Glu Pro
                 20                  25                  30

Pro Pro Ile Pro Ala Glu Ser Ser Pro Leu Leu Asn Glu Val Arg Gln
            35                  40                  45

Gly Val Arg Ser Arg Val Arg Arg Pro Pro Gly His Asn Gln Pro His
        50                  55                  60

Tyr Ala Leu Ala Val Arg Glu Pro Arg Gln Ser Thr Phe Arg Arg Ile
 65                  70                  75                  80

Leu Glu Leu Phe Glu Glu Met Leu Lys Arg Leu Gln Gln Arg Trp Arg
                 85                  90                  95

Gly Ala Leu Ala Trp Val Gln Glu Arg Ala Ala Ala Cys Phe Arg Gly
            100                 105                 110

Leu Cys Arg Ala Leu Glu Ala Phe Trp Ser Leu Val Gln Ser Phe Cys
        115                 120                 125
```

```
Ser Ser Met Gly His Ala Phe Gly Ser Val Ile Gln Val
    130                 135                 140

<210> SEQ ID NO 27
<211> LENGTH: 603
<212> TYPE: DNA
<213> ORGANISM: Sus scrofa

<400> SEQUENCE: 27
atgacttgga ggggaactga gcggccaggc ccagcccctg ggaaaagtcc tggggtctgt    60
ggggctgttg gcaggaaagc agcctgtgtc caaggcgggg catgaggggg gtgtctgcca   120
ccaggactct cccaaaggca gggcctcagc caaggtcagg actggggctg cctctcccca   180
ggcgggtccc tgaaccaccc cccatccctg cagaatccag tcctctgctc aacgaagtcc   240
ggcagggagt ccgttctaga gtccgaaggc ctcctggcca caaccagcca cattatgcgc   300
tagcggtccg ggagcccagg cagagcactt tcagacgcat ccttgagctg tttgaggaaa   360
tgctgaagcg cctgcagcag aggtggaggg gtgccctggc ttgggtgcag gaaagggctg   420
ctgcctgctt ccggggcttg tgcagggccc ttgaagcttt ctggagcctg gtgcagagtt   480
tttgctcctc catggggcac gccttcggga gtgtcatcca ggtctaaggt gctccaggtg   540
aaataagagt tctagagca caacctcccc ctgccttggc taaaaaggca gctgtaagcc   600
ttt                                                                603
```